United States Patent
Bache et al.

(10) Patent No.: US 9,962,273 B2
(45) Date of Patent: May 8, 2018

(54) ADJUSTABLE SOCKET SYSTEM

(71) Applicant: Ossur Iceland ehf, Reykjavik (IS)

(72) Inventors: Andrew Bache, Reykjavik (IS); Egill Sveinbjorn Egilsson, Reykjavik (IS); Linda Ros Birgisdottir, Reykjavik (IS); Dana Stewart Marlin, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days. days.

(21) Appl. No.: 15/151,204

(22) Filed: May 10, 2016

(65) Prior Publication Data
US 2016/0331562 A1    Nov. 17, 2016

Related U.S. Application Data

(60) Provisional application No. 62/160,668, filed on May 13, 2015.

(51) Int. Cl.
*A61F 2/50* (2006.01)
*A61F 2/78* (2006.01)
*A61F 2/80* (2006.01)

(52) U.S. Cl.
CPC .............. *A61F 2/80* (2013.01); *A61F 2/78* (2013.01); *A61F 2002/503* (2013.01); *A61F 2002/5026* (2013.01); *A61F 2002/5027* (2013.01)

(58) Field of Classification Search
CPC ...... A61F 2/76; A61F 2/78; A61F 2/80; A61F 2002/5016; A61F 2002/5021;
(Continued)

(56) References Cited

U.S. PATENT DOCUMENTS

| 37,282 A | 1/1863 | Engelbrecht et al. |
| 51,593 A | 12/1865 | Jewett |

(Continued)

FOREIGN PATENT DOCUMENTS

| CA | 2854799 A1 | 5/2013 |
| CA | 2889617 A1 | 5/2014 |

(Continued)

OTHER PUBLICATIONS

International Search Report from PCT Application No. PCT/2016/031615, dated Jul. 12, 2016.
(Continued)

*Primary Examiner* — Thomas J Sweet
*Assistant Examiner* — Christine Bahena
(74) *Attorney, Agent, or Firm* — Workman Nydegger

(57) ABSTRACT

An adjustable socket system includes a distal portion and proximal portion. An axis extends between the distal and proximal portions. A plurality of struts are connected to the distal portion and distributed circumferentially about the axis. The struts at least in part define a receiving volume adapted to receive a residual limb and are movable between an expanded configuration in which at least some of the struts are moved radially outward relative to the axis to loosen the fit of the adjustable system, and a closed configuration in which at least some of the struts are moved radially inward relative to the expanded configuration to tighten the fit of the adjustable socket system. A tightening system is operatively connected to the struts and arranged to tighten and loosen the fit of the adjustable socket system on one or more areas of the residual limb.

16 Claims, 13 Drawing Sheets

(58) Field of Classification Search
CPC ...... A61F 2002/5023; A61F 2002/5026; A61F 2002/5027; A61F 2002/5036; A61F 2002/5083; A61F 2002/5084; A61F 2002/509; A61F 2002/7862; A61F 2002/802; A61F 2002/805; A61F 2002/807; A61F 3/00; A61F 4/00; A61F 5/01; A61F 5/0102; A61F 5/0116; A61F 2005/0167

See application file for complete search history.

(56) References Cited

U.S. PATENT DOCUMENTS

| | | | |
|---|---|---|---|
| 366,494 A | 7/1887 | Marks | |
| 470,431 A | 3/1892 | Marks | |
| 1,066,605 A | 7/1913 | Hanger | |
| 1,082,256 A | 12/1913 | Apgar | |
| 1,144,681 A | 6/1915 | Apgar | |
| 1,861,311 A | 5/1932 | Logan | |
| 1,893,853 A | 1/1933 | Tullis | |
| 2,025,835 A | 12/1935 | Trautman | |
| 2,229,728 A | 1/1941 | Eddels | |
| 2,634,424 A | 4/1953 | O'Gorman | |
| 2,669,728 A | 2/1954 | Ritchie | |
| 2,759,271 A | 8/1956 | Von Duyke | |
| 2,908,016 A | 10/1959 | Botko | |
| 2,949,674 A | 8/1960 | Wexler | |
| 3,678,587 A | 7/1972 | Madden | |
| 4,128,903 A | 12/1978 | Marsh et al. | |
| 4,161,042 A | 7/1979 | Cottingham et al. | |
| 4,225,982 A | 10/1980 | Cochrane et al. | |
| 4,268,922 A | 5/1981 | Marsh et al. | |
| 4,283,800 A * | 8/1981 | Wilson | A61F 2/64 403/97 |
| 4,300,245 A | 11/1981 | Saunders | |
| 4,459,709 A | 7/1984 | Leal et al. | |
| 4,704,129 A | 11/1987 | Massey | |
| 4,715,124 A | 12/1987 | Harrington | |
| 4,783,293 A | 11/1988 | Wellershaus et al. | |
| 4,842,608 A | 6/1989 | Marx et al. | |
| 4,872,879 A | 10/1989 | Shamp | |
| 4,921,502 A | 5/1990 | Shamp | |
| 4,938,775 A | 7/1990 | Morgan | |
| 4,988,360 A | 1/1991 | Shamp | |
| 5,003,969 A | 4/1991 | Azer et al. | |
| 5,014,441 A | 5/1991 | Pratt | |
| 5,108,456 A | 4/1992 | Coonan, III | |
| 5,133,777 A | 7/1992 | Arbogast et al. | |
| 5,168,635 A | 12/1992 | Hoffman | |
| 5,201,773 A | 4/1993 | Carideo, Jr. | |
| 5,201,775 A | 4/1993 | Arbogast et al. | |
| 5,246,464 A | 9/1993 | Sabolich | |
| 5,312,669 A | 5/1994 | Bedard | |
| 5,424,782 A | 6/1995 | Aoki | |
| 5,503,543 A | 4/1996 | Laghi | |
| 5,520,529 A | 5/1996 | Heckel | |
| 5,529,575 A | 6/1996 | Klotz | |
| 5,529,576 A | 6/1996 | Lundt et al. | |
| 5,545,231 A | 8/1996 | Houser | |
| 5,571,209 A | 11/1996 | Brown, Sr. | |
| 5,651,792 A | 7/1997 | Telikicherla | |
| 5,652,053 A | 7/1997 | Liegeois | |
| 5,653,766 A | 8/1997 | Naser | |
| 5,718,925 A | 2/1998 | Kristinsson et al. | |
| 5,724,714 A | 3/1998 | Love | |
| 5,728,165 A | 3/1998 | Brown, Sr. | |
| 5,800,565 A | 9/1998 | Biedermann | |
| 5,824,111 A | 10/1998 | Schall et al. | |
| 5,885,509 A | 3/1999 | Kristinsson | |
| 5,888,215 A | 3/1999 | Roos et al. | |
| 5,888,217 A | 3/1999 | Slemker | |
| 5,897,517 A | 4/1999 | Laghi | |
| 6,033,440 A | 3/2000 | Schall et al. | |
| 6,051,026 A | 4/2000 | Biedermann et al. | |
| 6,206,932 B1 | 3/2001 | Johnson | |
| 6,228,124 B1 | 5/2001 | Slemker et al. | |
| 6,231,618 B1 | 5/2001 | Schall et al. | |
| 6,368,357 B1 | 4/2002 | Schon et al. | |
| 6,406,499 B1 | 6/2002 | Kania | |
| 6,444,282 B1 | 9/2002 | Shirer | |
| 6,458,163 B1 | 10/2002 | Slemker et al. | |
| 6,497,028 B1 | 12/2002 | Rothschild et al. | |
| 6,500,210 B1 | 12/2002 | Sabolich et al. | |
| 6,557,177 B2 | 5/2003 | Hochmuth | |
| 6,669,736 B2 | 12/2003 | Slemker et al. | |
| 6,700,563 B1 | 3/2004 | Koizumi | |
| 6,761,743 B1 | 7/2004 | Johnson | |
| 6,793,682 B1 | 9/2004 | Mantelmacher | |
| 6,942,703 B2 | 9/2005 | Carstens | |
| 6,974,484 B2 | 12/2005 | Caspers | |
| 6,991,657 B1 | 1/2006 | Price, Jr. | |
| 7,090,700 B2 | 8/2006 | Curtis | |
| 7,094,212 B2 | 8/2006 | Karason et al. | |
| 7,097,799 B1 | 8/2006 | Burton | |
| 7,105,122 B2 | 9/2006 | Karason | |
| 7,118,602 B2 | 10/2006 | Bjarnason | |
| 7,172,714 B2 | 2/2007 | Jacobson | |
| 7,240,414 B2 | 7/2007 | Taylor, Sr. | |
| 7,288,116 B2 | 10/2007 | Ikeda | |
| 7,300,466 B1 | 11/2007 | Martin | |
| 7,318,504 B2 | 1/2008 | Vitale et al. | |
| 7,338,532 B2 | 3/2008 | Haberman et al. | |
| 7,344,567 B2 | 3/2008 | Slemker | |
| 7,402,265 B2 | 7/2008 | Jacobson | |
| 7,479,163 B2 | 1/2009 | Slemker et al. | |
| 7,488,349 B2 | 2/2009 | Einarsson | |
| 7,591,857 B2 | 9/2009 | Slemker et al. | |
| 7,658,720 B2 | 2/2010 | Johnson, III | |
| 7,727,284 B2 | 6/2010 | Warila | |
| 7,753,866 B2 | 7/2010 | Jackovitch | |
| 7,762,973 B2 | 7/2010 | Einarsson et al. | |
| 7,867,286 B2 | 1/2011 | Einarsson | |
| 7,980,921 B2 | 7/2011 | Saravanos | |
| 7,985,192 B2 | 7/2011 | Sheehan et al. | |
| 8,007,544 B2 | 8/2011 | Jonsson et al. | |
| 8,083,807 B2 | 12/2011 | Auberger et al. | |
| 8,088,320 B1 | 1/2012 | Bedard | |
| 8,116,900 B2 | 2/2012 | Slemker et al. | |
| 8,123,818 B2 | 2/2012 | Bjarnason et al. | |
| 8,142,517 B2 | 3/2012 | Horie | |
| 8,303,527 B2 | 11/2012 | Joseph | |
| 8,308,815 B2 | 11/2012 | McCarthy | |
| 8,323,353 B1 | 12/2012 | Alley et al. | |
| 8,382,852 B2 | 2/2013 | Laghi | |
| 8,403,993 B2 | 3/2013 | Aram et al. | |
| 8,414,658 B2 | 4/2013 | Johnson et al. | |
| 8,470,050 B2 | 6/2013 | Dillingham | |
| 8,480,758 B2 | 7/2013 | McLeod | |
| 8,535,389 B2 | 9/2013 | McKinney | |
| 8,576,250 B2 | 11/2013 | Sabiston et al. | |
| 8,795,385 B2 | 8/2014 | Bache | |
| 8,978,224 B2 | 3/2015 | Hurley et al. | |
| 9,044,349 B2 | 6/2015 | Hurley et al. | |
| 9,050,202 B2 | 6/2015 | Bache et al. | |
| 9,248,033 B2 | 2/2016 | Bache | |
| 9,283,093 B2 | 3/2016 | Alley | |
| 9,468,542 B2 | 10/2016 | Hurley et al. | |
| 9,468,543 B2 | 10/2016 | Hurley et al. | |
| 9,474,633 B2 | 10/2016 | Williams et al. | |
| 9,549,828 B2 | 1/2017 | Hurley et al. | |
| 9,572,691 B2 | 2/2017 | Pacanowsky et al. | |
| 2002/0099450 A1 | 7/2002 | Dean, Jr. et al. | |
| 2003/0181990 A1 | 9/2003 | Phillips | |
| 2004/0260402 A1 | 12/2004 | Baldini et al. | |
| 2005/0278039 A1 | 12/2005 | Nobbe | |
| 2006/0009860 A1 | 1/2006 | Price, Jr. | |
| 2006/0020348 A1 | 1/2006 | Slemker et al. | |
| 2006/0135902 A1 | 6/2006 | Ingimundarson et al. | |
| 2007/0004993 A1 | 1/2007 | Coppens et al. | |
| 2007/0078523 A1 | 4/2007 | Kholwadwala et al. | |
| 2007/0152379 A1 | 7/2007 | Jacobson | |
| 2007/0298075 A1 | 12/2007 | Borgia et al. | |
| 2008/0066272 A1 | 3/2008 | Hammerslag et al. | |
| 2008/0269914 A1 | 10/2008 | Coppens et al. | |

(56) References Cited

U.S. PATENT DOCUMENTS

| | | |
|---|---|---|
| 2009/0036999 A1 | 2/2009 | Egilsson et al. |
| 2009/0076625 A1 | 3/2009 | Groves et al. |
| 2009/0105844 A1 | 4/2009 | Ortiz |
| 2009/0240344 A1 | 9/2009 | Colvin et al. |
| 2009/0287128 A1 | 11/2009 | Ingimundarson et al. |
| 2009/0299490 A1 | 12/2009 | Summit |
| 2010/0030344 A1 | 2/2010 | Hansen et al. |
| 2010/0036300 A1 | 2/2010 | Sheehan et al. |
| 2010/0036505 A1 | 2/2010 | Hassler |
| 2010/0082116 A1 | 4/2010 | Johnson et al. |
| 2010/0121464 A1 | 5/2010 | Mantelmacher |
| 2010/0160722 A1 | 6/2010 | Kuyava et al. |
| 2010/0191348 A1 | 7/2010 | Kettwig et al. |
| 2010/0274364 A1 | 10/2010 | Pacanowsky et al. |
| 2011/0029096 A1 | 2/2011 | Laghi |
| 2011/0035027 A1 | 2/2011 | McCarthy |
| 2011/0071647 A1 | 3/2011 | Mahon |
| 2011/0114635 A1 | 5/2011 | Sheehan |
| 2011/0232837 A9 | 9/2011 | Ottleben |
| 2011/0320010 A1 | 12/2011 | Vo |
| 2012/0022667 A1 | 1/2012 | Accinni et al. |
| 2012/0041567 A1 | 2/2012 | Cornell |
| 2012/0095570 A1 | 4/2012 | Marquette |
| 2012/0101417 A1 | 4/2012 | Joseph |
| 2012/0101597 A1 | 4/2012 | Bache |
| 2012/0143077 A1 | 6/2012 | Sanders et al. |
| 2012/0165956 A1 | 6/2012 | Li |
| 2012/0191218 A1 | 7/2012 | McCarthy |
| 2012/0215324 A1 | 8/2012 | King |
| 2012/0253475 A1 | 10/2012 | Kelley et al. |
| 2012/0259434 A1 | 10/2012 | Dillingham |
| 2012/0271210 A1 | 10/2012 | Galea et al. |
| 2012/0271433 A1 | 10/2012 | Galea et al. |
| 2012/0283846 A1 | 11/2012 | Janssen et al. |
| 2012/0293411 A1 | 11/2012 | Leithinger et al. |
| 2013/0123940 A1 | 5/2013 | Hurley et al. |
| 2013/0192071 A1 | 8/2013 | Esposito et al. |
| 2013/0197318 A1 | 8/2013 | Herr et al. |
| 2013/0245785 A1 | 9/2013 | Accini et al. |
| 2013/0282141 A1 | 10/2013 | Herr et al. |
| 2014/0031953 A1 | 1/2014 | MacKenzie |
| 2014/0121783 A1 | 5/2014 | Alley |
| 2014/0135946 A1 | 5/2014 | Hurley et al. |
| 2014/0149082 A1 | 5/2014 | Sanders et al. |
| 2014/0227584 A1 | 9/2014 | Hurley et al. |
| 2014/0277585 A1 | 9/2014 | Kelley et al. |
| 2015/0105867 A1 | 4/2015 | Novak |
| 2015/0168943 A1 | 6/2015 | Hurley et al. |
| 2015/0190252 A1 | 6/2015 | Hurley et al. |
| 2015/0230945 A1 | 8/2015 | Bache et al. |
| 2015/0257905 A1 | 9/2015 | Bache |
| 2015/0265434 A1 | 9/2015 | Hurley et al. |
| 2015/0313729 A1 | 11/2015 | Williams et al. |
| 2015/0313730 A1 | 11/2015 | Hurley et al. |
| 2015/0352775 A1 | 12/2015 | Geshlider et al. |
| 2016/0000586 A1 | 1/2016 | Hurley et al. |
| 2016/0000587 A1 | 1/2016 | Hurley et al. |
| 2016/0143752 A1 | 5/2016 | Hurley et al. |
| 2016/0158035 A1 | 6/2016 | Alley |
| 2017/0027718 A1 | 2/2017 | Williams et al. |
| 2017/0128238 A1 | 5/2017 | Hurley et al. |
| 2017/0156896 A1 | 6/2017 | Alley |

FOREIGN PATENT DOCUMENTS

| | | |
|---|---|---|
| CN | 104053416 B | 11/2016 |
| DE | 319623 C | 3/1920 |
| DE | 102014001000 A1 | 7/2014 |
| EP | 0204407 A2 | 12/1986 |
| EP | 1433447 A2 | 6/2004 |
| EP | 2629705 A1 | 8/2013 |
| EP | 2775967 A1 | 9/2014 |
| EP | 2914221 A1 | 9/2015 |
| EP | 2967925 A1 | 1/2016 |
| EP | 2866747 B1 | 2/2017 |
| GB | 127 451 A | 6/1919 |
| GB | 2080114 A | 2/1982 |
| WO | 91/16019 A1 | 10/1991 |
| WO | 98/12994 A1 | 4/1998 |
| WO | 0003665 A1 | 1/2000 |
| WO | 0030572 A1 | 6/2000 |
| WO | 2007/035875 A2 | 3/2007 |
| WO | 2008/116025 A2 | 9/2008 |
| WO | 2009/093020 A2 | 7/2009 |
| WO | 2012/021823 A1 | 2/2012 |
| WO | 2012054700 A1 | 4/2012 |
| WO | 2013/071308 A1 | 5/2013 |
| WO | 2014004709 A1 | 1/2014 |
| WO | 2014005071 A1 | 1/2014 |
| WO | 2014068269 A1 | 5/2014 |
| WO | 2014070666 A1 | 5/2014 |
| WO | 2014153244 A1 | 9/2014 |
| WO | 2015143249 A1 | 9/2015 |

OTHER PUBLICATIONS

International Search Report and Written Opinion Issued of PCT/US2011/057043, dated Jan. 27, 2012, 10 pages.
Initial and Interim Prostheses [Retrieved from Internet on Feb. 11, 2013], <URL:http://www.ottobockus.com/cps/rde/xbcr/ob_us_en/08cat_4.pdf>. Published in Prosthetics Lower Extremities 2008, see contents page <URL:http://www.ottobockus.com/cps/rde/xbcr/ob_us_en/08cat_1.pdf> pp. 24-31.
International Search Report from Corresponding PCT Application No. PCT/US2013/048675, dated Oct. 9, 2013.
Manual: "Socket Evaluation System with the Rapid Adjustment Pylon", [retrieved from the internet on May 22, 2014], <URL:http://www.fillauer.com>; 4 pages.
Alley, "The High-Fidelity Interface: Skeletal Stabilization Through Alternating Soft Tissue Compression and Release", Proceedings of the 2011 MyoElectric Controls/Powered Prosthetics Symposium Fredericton, New Brunswick, Canada, Aug. 2011. 3 Pages.
Andrysek, "Lower-Limb Prosthetic Technologies in the Developing World: A Review of Literature from 1994-2010", Prosthetics and Orthotics International, Cardiff, Wales, UK; vol. 34, No. 4, Dec. 2010; pp. 378-398.
Conn, "Materials Science: A Look at Some of the Substances on the Market for Device Fabrication", O&P Almanac, Jun. 2012, pp. 28-31; http://wwww.allardusa.com/pdf/articles/Materials%20Science%20Article%20-%20June%202012%20O%26P%20Almanac.pdf.
Fairley, M. "From Academia to the Developing World: Student Engineers Create Collaborative Technologies", The O&P Edge Magazine, OandP.com, Mar. 2011, pp. 1-9. Downloaded from http://www.oandp.com/articles/2011-05-03.asp.
Fairley, M. "M.A.S. Socket: A Transfemoral Revolution", The O&P Edge, Jun. 2004, www.oandp.com/articles/2004-06_03.asp. 5 Pages.
"COMFIL—Thermo Formable Composite Technique", Fillaur LLC and Centri, Fabrication Manuel, Jun. 15, 2012, pp. 1-13.
Gard, S.A. "Overview of Lower Limb Prosthetics Research", WRAMC and the VA Orthopedic & Prosthetic Workshop Arlington, VA, Nov. 17-18, 2003, pp. 1-49.
Geil, M.D., "Consistency, Precision, and Accuracy of Optical and Electromagnetic Shape-Capturing Systems for Digital Measurement of Residual-limb Anthropometrics of Persons With Transtibial Amputation", Journal of Rehabilitation Research and Development, vol. 44, No. 4, 2007; pp. 515-524.
Gleave, "A Plastic Socket and Stump Casting Technique for Above-Knee Prostheses", Orthopaedic and Prosthetic Appliance Department, Hong Kong Government Medical Department, The Journal of Bone and Joint Surgery, vol. 47B, No. 1, Feb. 1965, pp. 100-103.
Gerschutz, et al., "Mechanical Evaluation of Direct Manufactured Prosthetic Sockets", American Academy of Orthotists & Prosthetists, 38th Academy Annual Meeting and Scientific Symposium, U.S.A., Mar. 21-24, 2012; downloaded from http://www.oandp.org/publications/jop/2012/2012-19.pdf. 1 page.
Greenwald, et al., "Volume Management: Smart Variable Geometry Socket (SVGS) Technology for Lower-Limb Prostheses", American

(56) References Cited

OTHER PUBLICATIONS

Academy of Orthotists & Prosthetists, vol. 15, No. 3, 2003, pp. 107-112.
Hong, et al, "Dynamic Moisture Vapor Transfer through Textiles: Part I: Clothing Hygrometry and the Influence of Fiber Type", Textile Research Journal, Thousand Oaks, California, U.S.A., Dec. 1988; 58: 697-706, Abstract. 1 Page.
Hwang, "Blooming Winner—Spark!", Spark Galleries, 2012/Spark/Concept,Spark Design Awards, 2012 3 Pages. Downloaded from http://www.sparkawards.com/galleriew/index.cfm?entry=9525D900-EoEF-59BD-46597D99 . . . .
Jana, "Designing a Cheaper, Simpler Prosthetic Arm", ZDNet, Nov. 14, 2011, pp. 1-5. Downloaded from http://www.2dnet.com/article/designing-a-cheaper-simpler-prosthetic-arm/.
Koike, et al., "The TC Double Socket Above-knee Prosthesis", Prosthetics and Orthotics International, vol. 5, 1981 pp. 129-134.
Krouskop, et al., "Computer-aided design of a prosthetic socket for an above-knee amputee", Journal of Rehabilitation Research and Development, vol. 24, No. 2 1987, pp. 31-38.
Manucharian, "An Investigation of Comfort Level Trend Differences Between the Hands-On Patellar Tendon Bearing and Hands-Off Hydrocast Transtibial Prosthetic Sockets", JPO: American academy of Orthotists & Prosthetists, Washington, D.C., U.S.A.; vol. 23, No. 3, 2011: pp. 124-140.
Otto Bock Healthcare LLP, "Initial and Interim Prostheses", Otto Bock Healthcare LLP, Prosthetics Lower Extremities 2008, Feb. 2013 pp. 1-8, www.ottobockus.com/cps/rde/xbcr/ob_us_en/08cat_I.pdf.
Otto Bock Healthcare LLP , "Ottobock: PU Resin Kit Polytol"; Downloaded Dec. 17, 2012 from http://www.ottobock.com/cps.rde/xchg/ob_com_en/hs.xs1/17414.html.
Sanders, et al., "Residual limb volume change: Systematic review of measurement and management", Journal of Rehabilitation Research & Development, 2011, vol. 48, No. 8, pp. 949-986.
Sathishkumar, et al., "A cost-effective, adjustable, femoral socket, temporary prosthesis for immediate rehabilitation of above-knee amputation", International Journal of Rehabilitation Research, Ljubljana, Slovenia, Mar. 2004, vol. 27, No. 1; pp. 71-74.
SBIR topic summary: "Pro-Active Dynamic Accommodating Socket", http://www.dodsbir.net/sitis/archieves_display_topic.asp?Bookmark=34570; downloaded Mar. 25, 2013, U.S. A. 3 pages.
Smith, "Silver Linings for O&P Devices", The Academy Today, vol. 1, No. 4: Oct. 2005, 4 Pages, Downloaded from, http://www.oandp.org/AcademyTODAY/20050ct/7.asp.
Spaeth, JP , "Laser Imaging and Computer-Aided Design and Computer-Aided Manufacture in Prosthetics and Orthotics", Physical Medicine and Rehabilitation Clinics of North America, Elsevier Publishing, Amsterdam, The Netherlands; Feb. 2006 pp. 245-263, Abstract. 2 pages.
Turner, "FIT for Everyone", Yanko Design—Form Beyond Junction, Jul. 17, 2015, pp. 1-10. Downloaded from http://www.yankodesign.com/2013/07/17/fit-for-erveryone/.
"Hanger ComfortFlex Socket System for Prosthetic Devices:" Downloaded Nov. 28, 2012 from http://www.hanger.com/prosthetics/services/Technology/Pages/ComfortFlex.asp pp. 1-2.
Wilson JR. "A Material for Direct Forming of Prosthetic Sockets", Artificial Limbs., vol. 4, No. 1, 1970, Downloaded from http://www.oandplibrary.org/al/1970_01_053.asp; downloaded Dec. 14, 2012. pp. 53-56.
Wilson, "Recent Advances in Above-Knee Prosthetics", Artificial Limbs, vol. 12, No. 2, 1968 pp. 1-27.
Wu, et al, "CIR sand casting system for trans-tibial socket", Prosthetics and Orthotics International, Aug. 2003: vol. 27, pp. 146-152.
Extended Search Report from European Patent Application No. 12847452.5, dated Jul. 21, 2015.
International Search Report for International Application No. PCT/US2012/064876, dated Feb. 19, 2013.
Written Opinion of the International Searching Authority for International Application No. PCT/US2012/064876, dated Feb. 19, 2013.
International Search Report for International Application No. PCT/US2014/029773, dated Jun. 13, 2014.
Written Opinion of the International Searching Authority for International Application No. PCT/US2014/029773,dated Jun. 13, 2014.
Written Opinion of the International Searching Authority for International Application No. PCT/US2014/043500, dated Aug. 14, 2014.
International Search Report for International Application No. PCT/US2014/043500, dated Aug. 18, 2014.
International Search Report for International Application No. PCT/US15/021611, dated Jun. 25, 2015.
Written Opinion of the International Searching Authority for International Application No. PCT/US15/021611, dated Jun. 25, 2015.
International Search Report for International Application No. PCT/US2014/070666, dated Mar. 31, 2015.
Written Opinion of the International Searching Authority for International Application No. PCT/US2014/070666, dated Mar. 31, 2015.
Quigley, Michael, "Prosthetic Management: Overview, Methods and Materials," Chapter 4, Atlas of Limb Prosthetics: Surgical, Prosthetic, and Rehabilitation Principles, Second Edition, 1992, 10 Pages. Downloaded from: http://www.oandplibrary.org/alp/chapot-01-asp.
Burgess, et al. "Immediate Post-Surgical Prosthetic Fitting", The Management of Lower-Extremity Amputations, Aug. 1969, pp. 42-51.
Compton, et al., "New Plastics for Forming Directly on the Patient", Prosthetics and Orthotics International, 1978, vol. 2, No. 1, pp. 43-47, Abstract. 3 Pages.
Fairley, "Socket Can Be Fabricated, Modified, Fitted—In One Hour", The O&P Edge, Jun. 2007. 5 Pages.
"Cut-4-Custom: Custom TLSO in Less Than an Hour", The O&P Edge, Oct. 2010. 2 Pages.
"Remoldable Prosthetics", InstaMorph Moldable Plastic, http://instamorph.com/wp-content/uploads/legcast1.png, Retrieved, May 10, 2016. 3 Pages.

* cited by examiner

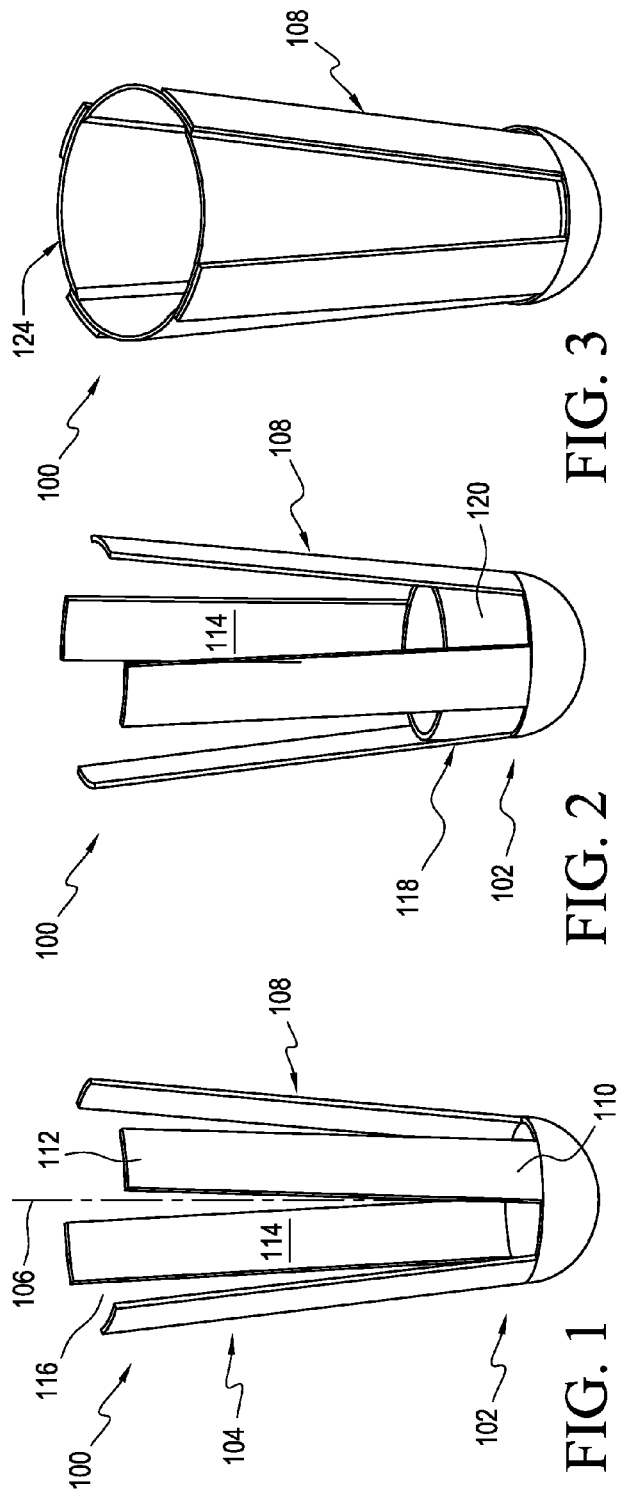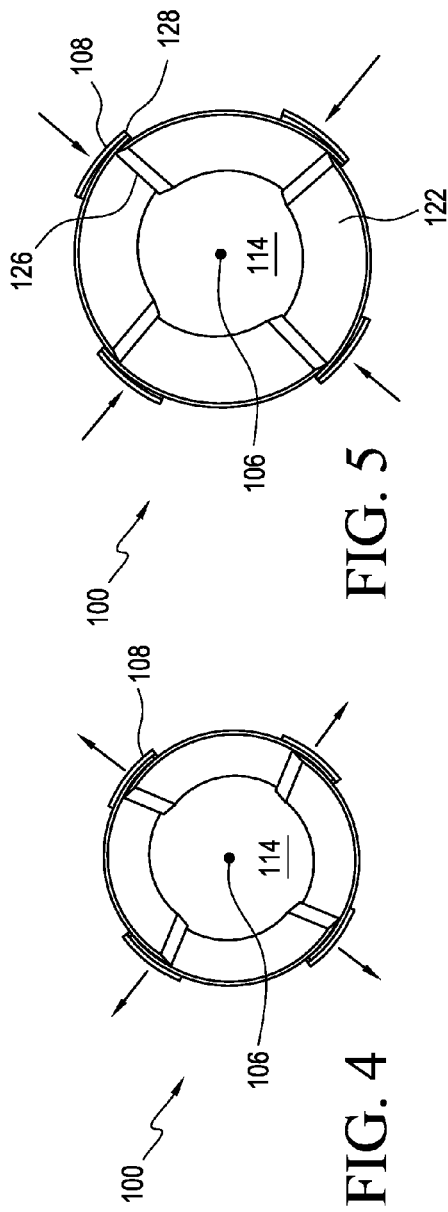

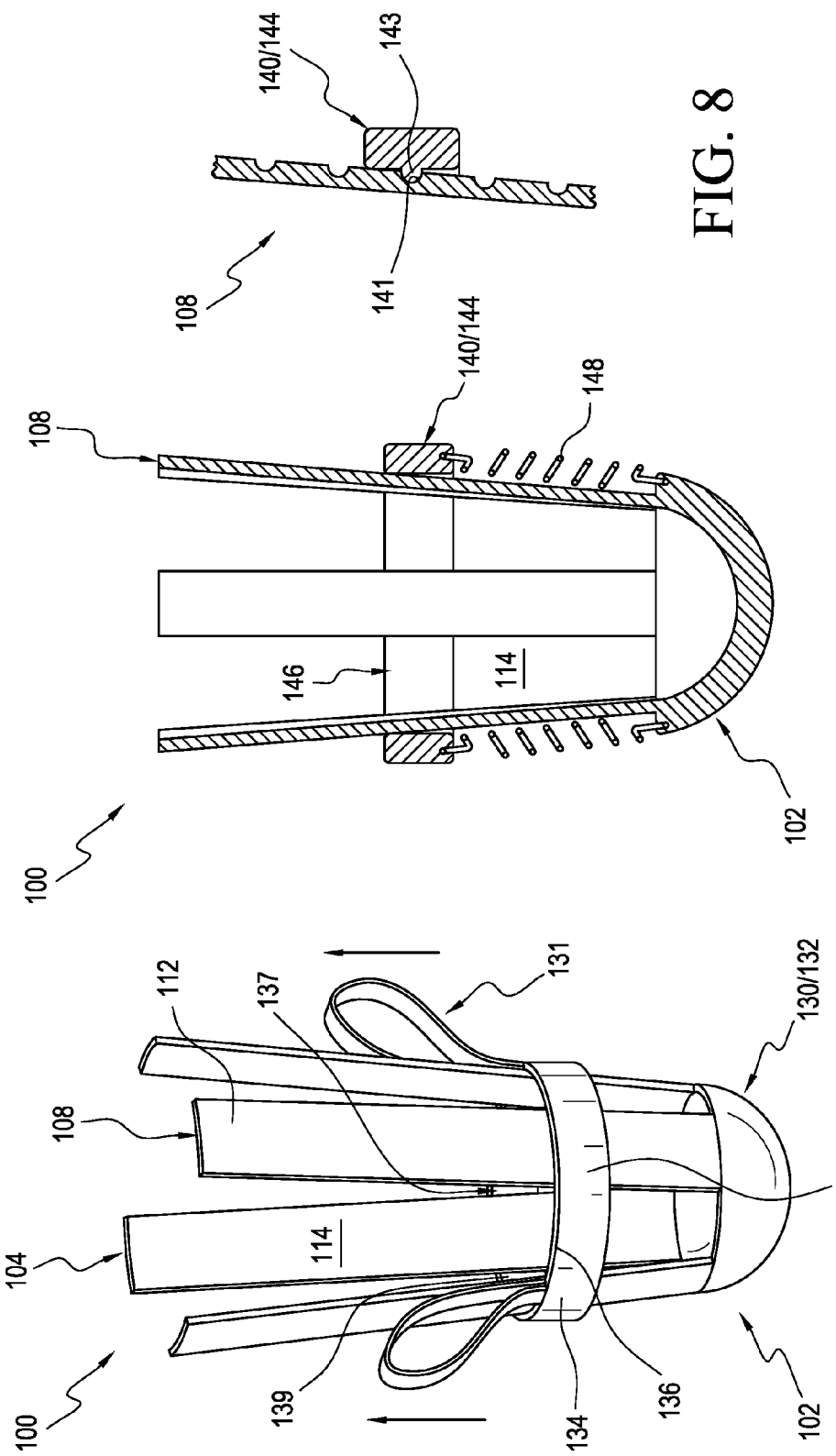

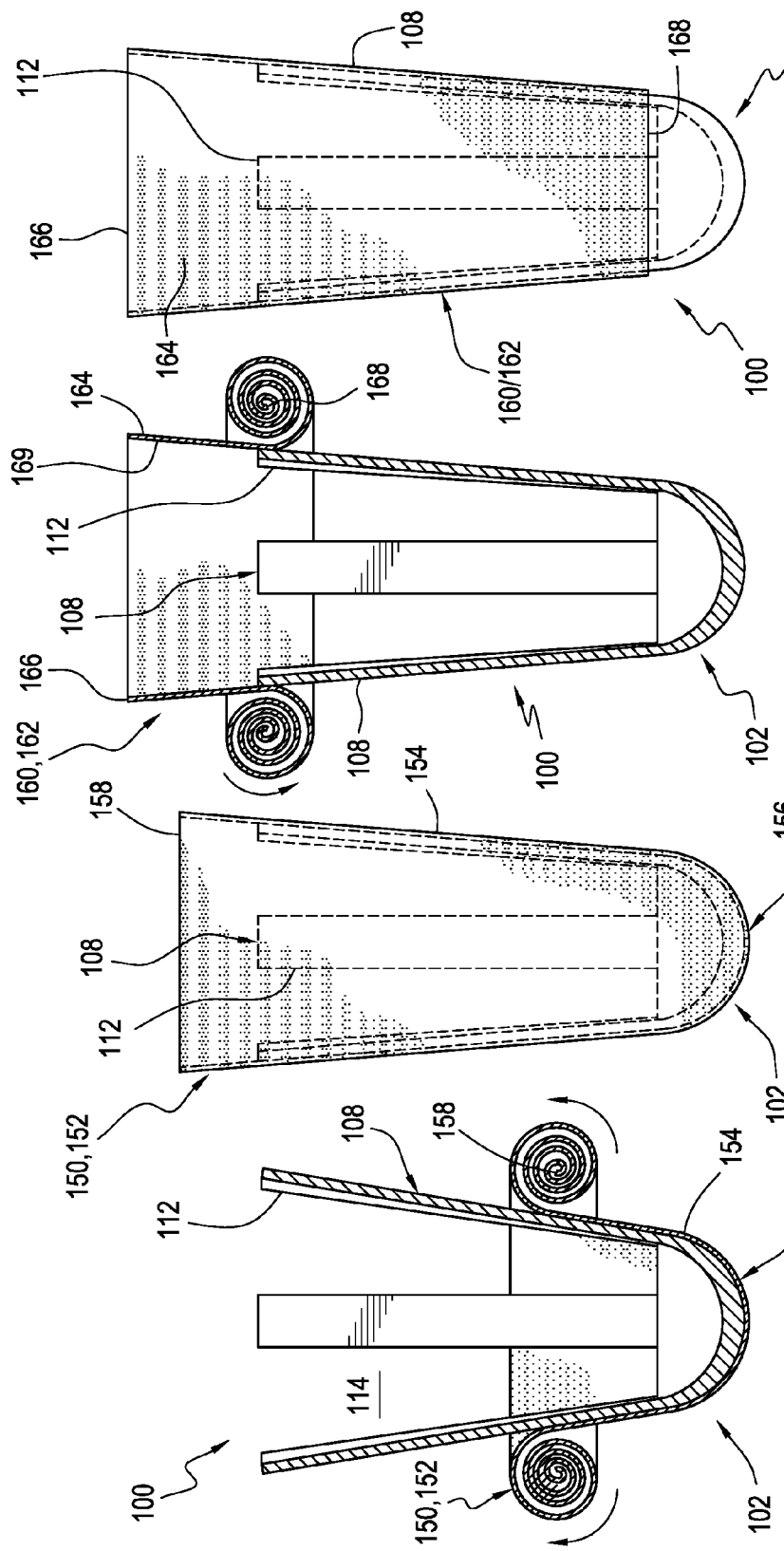

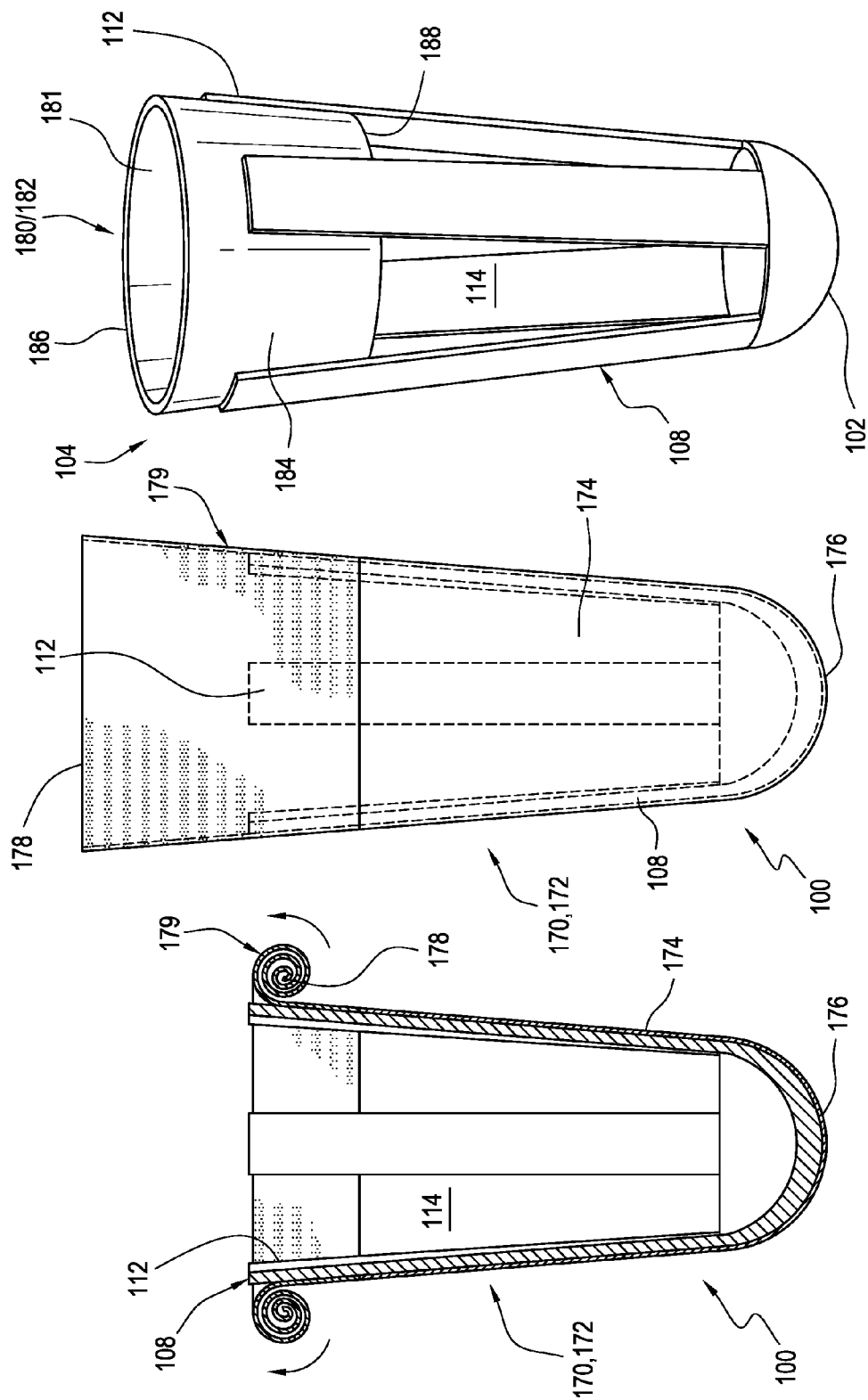

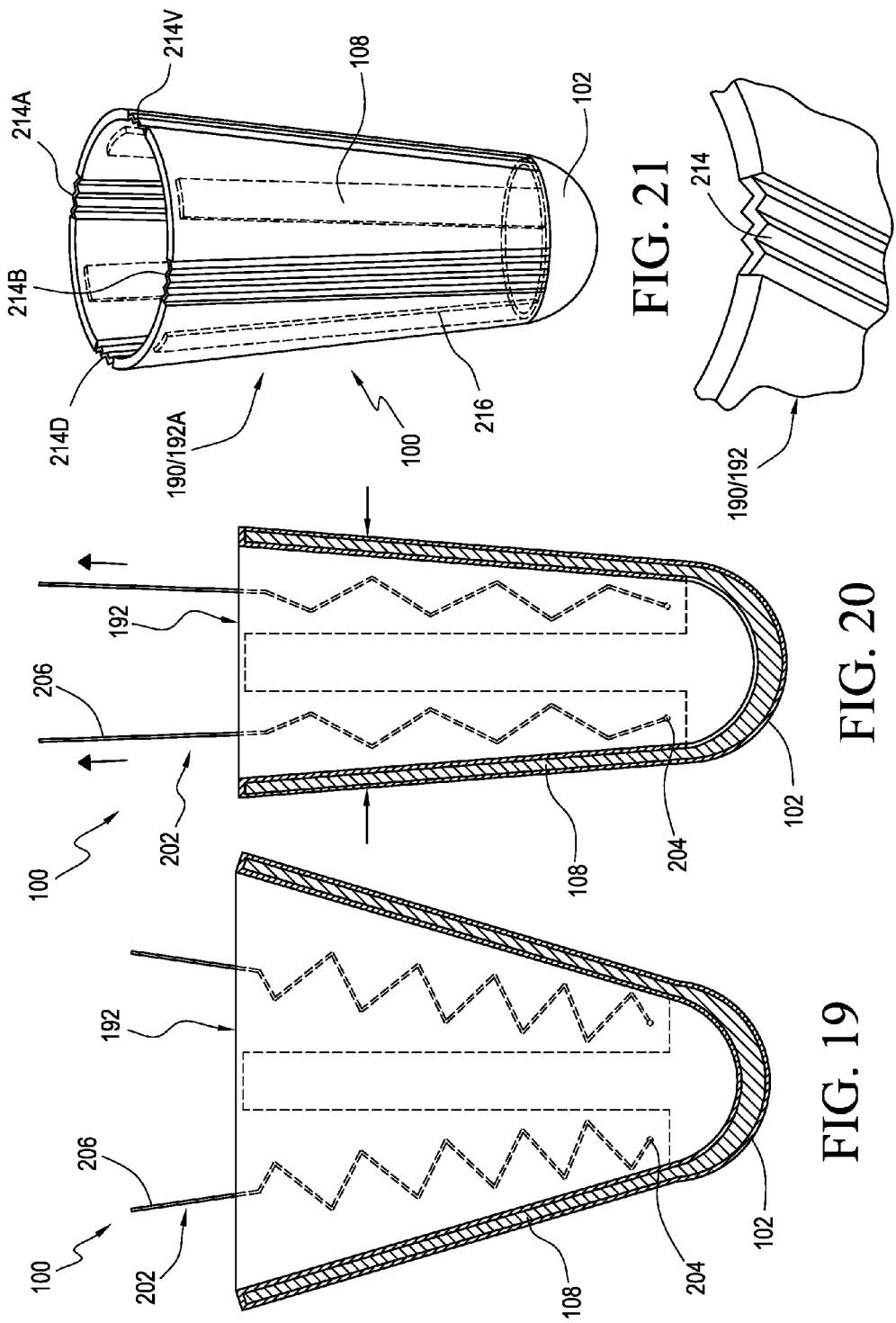

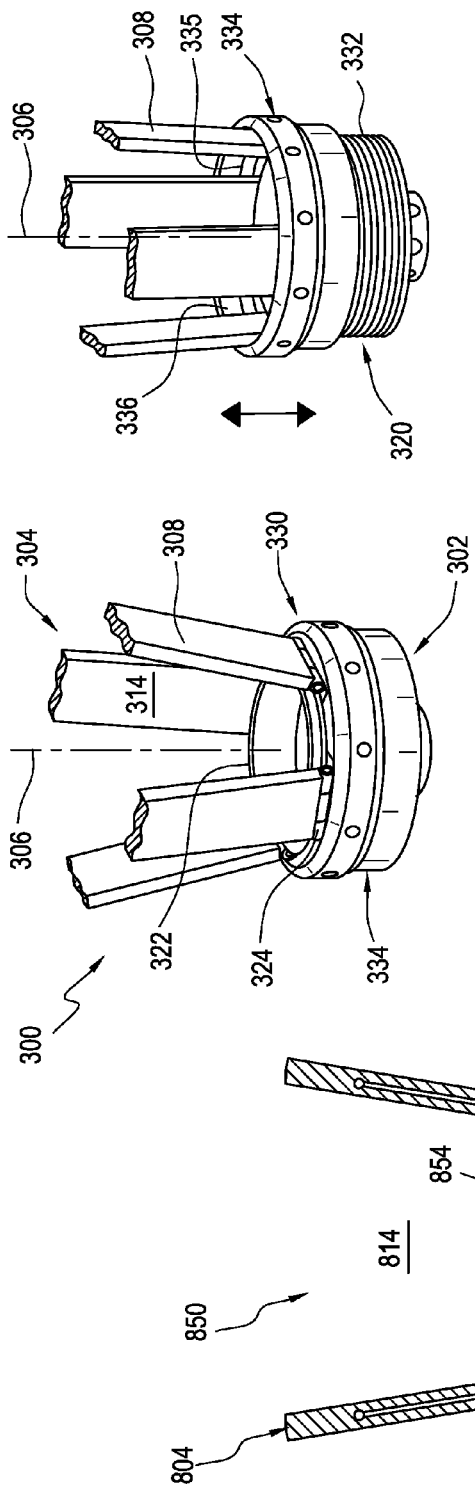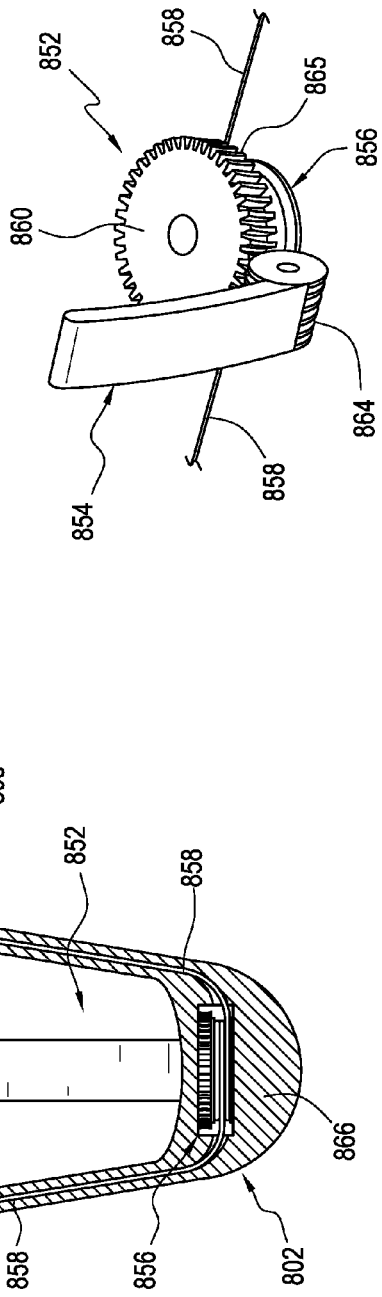

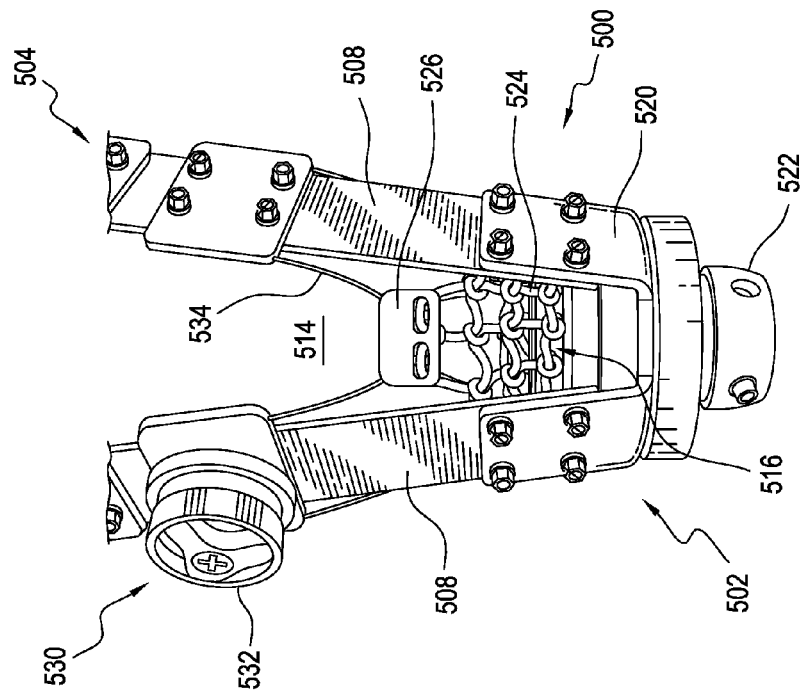
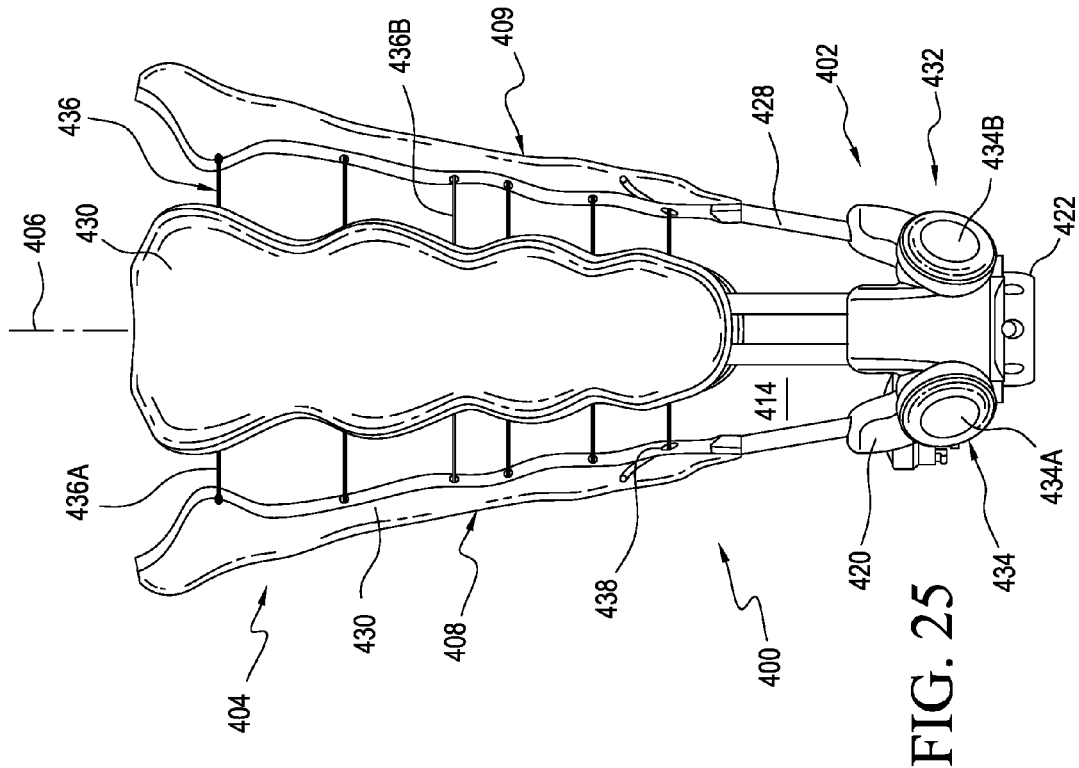
FIG. 26
FIG. 25

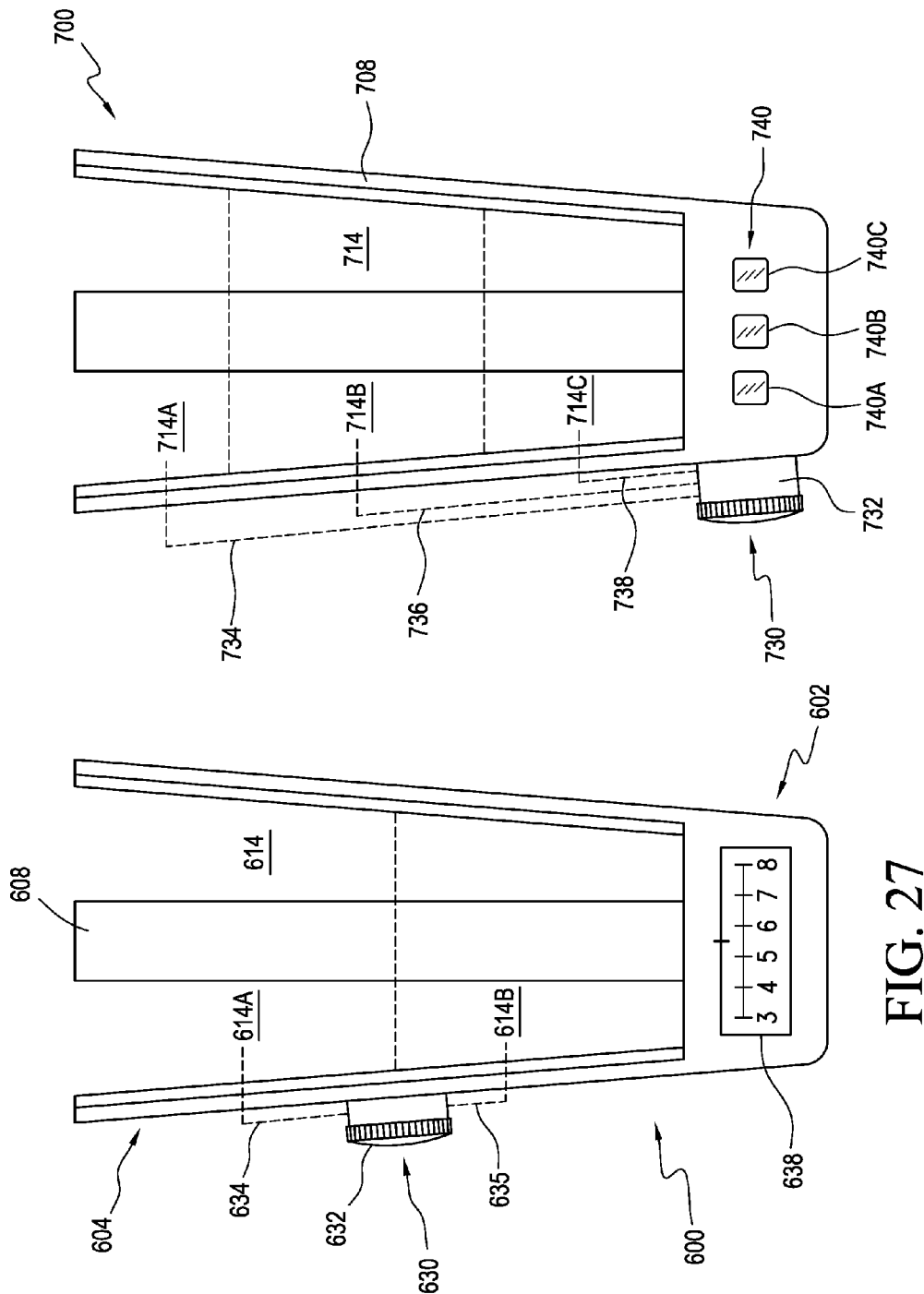

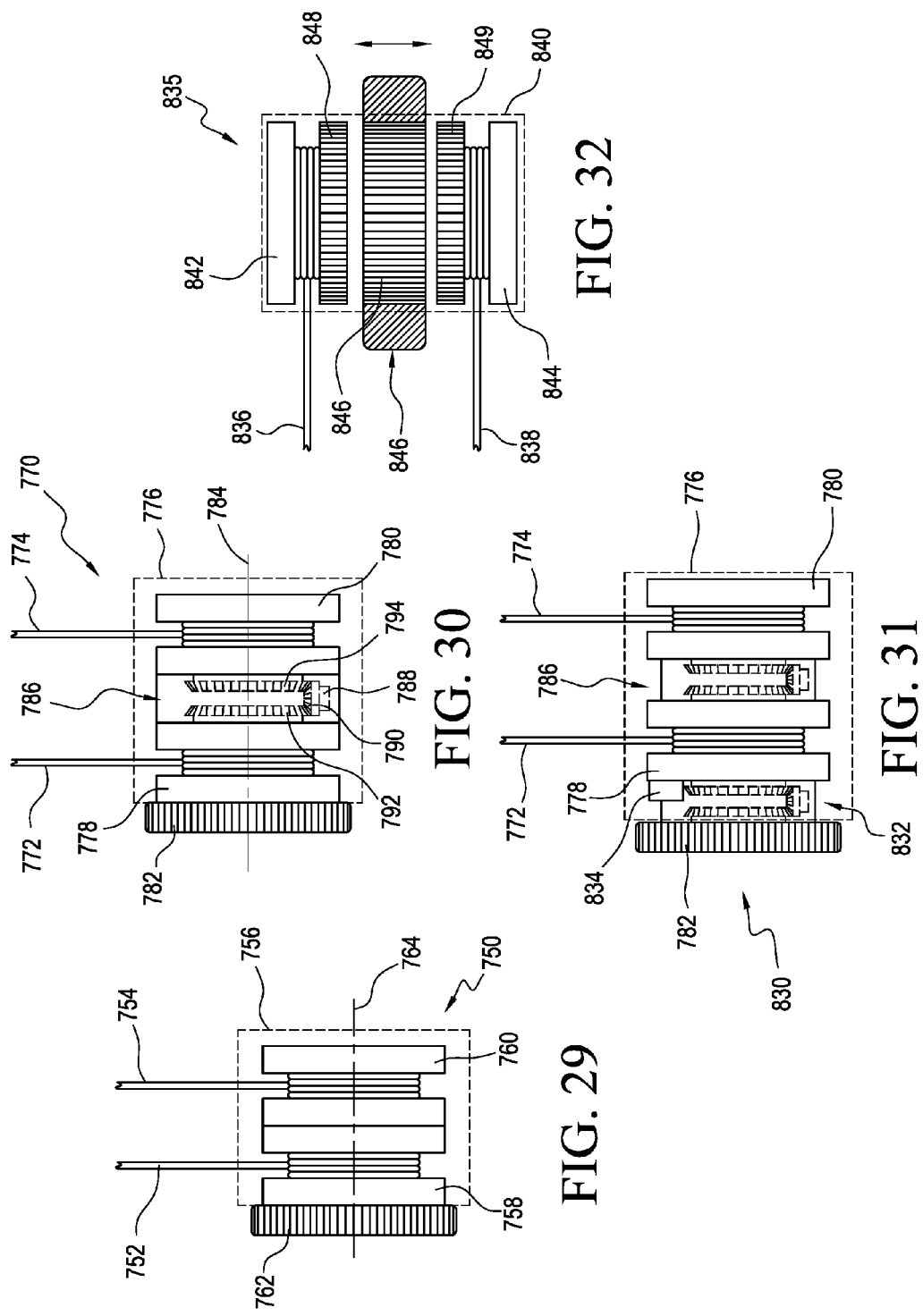

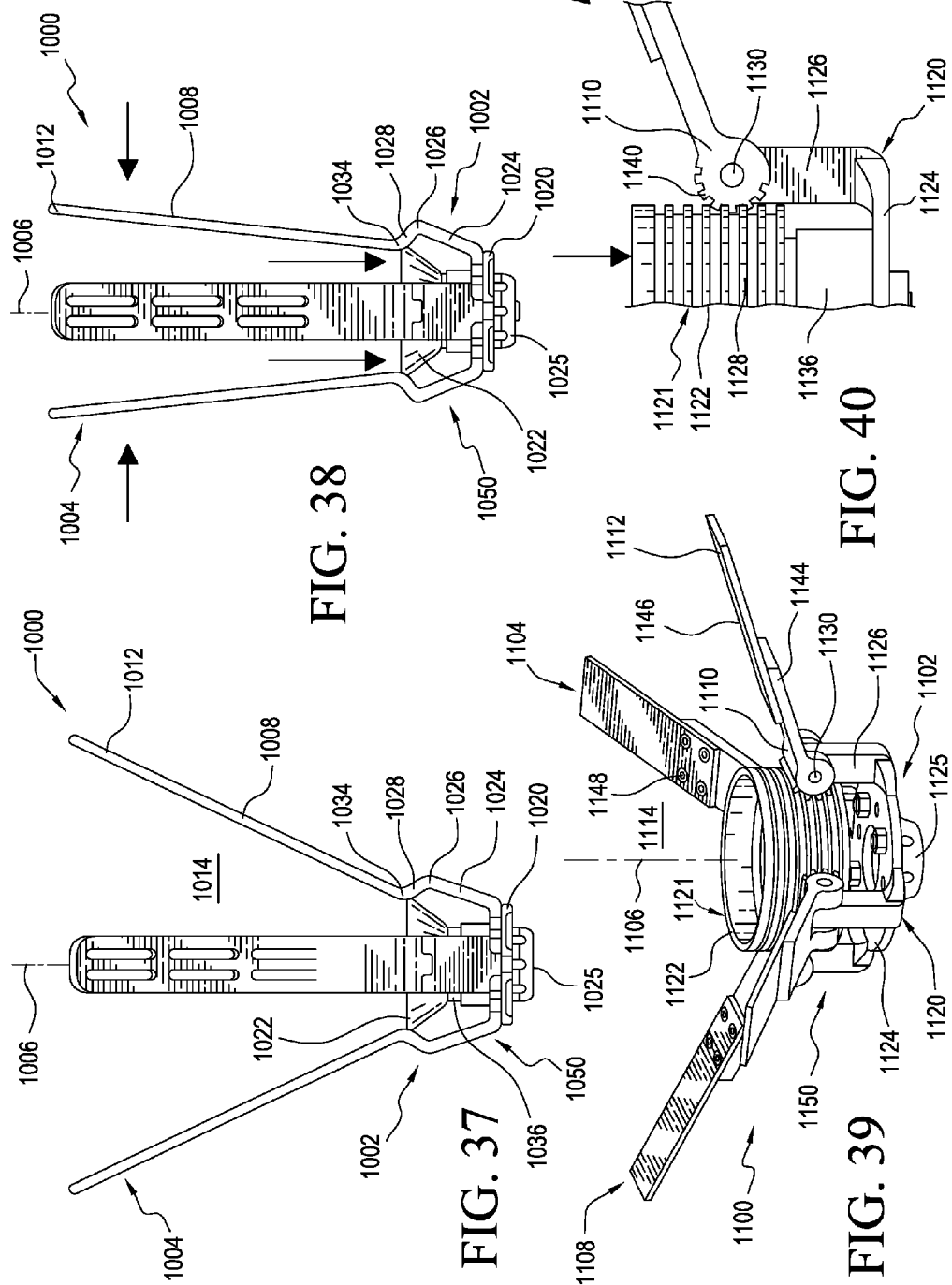

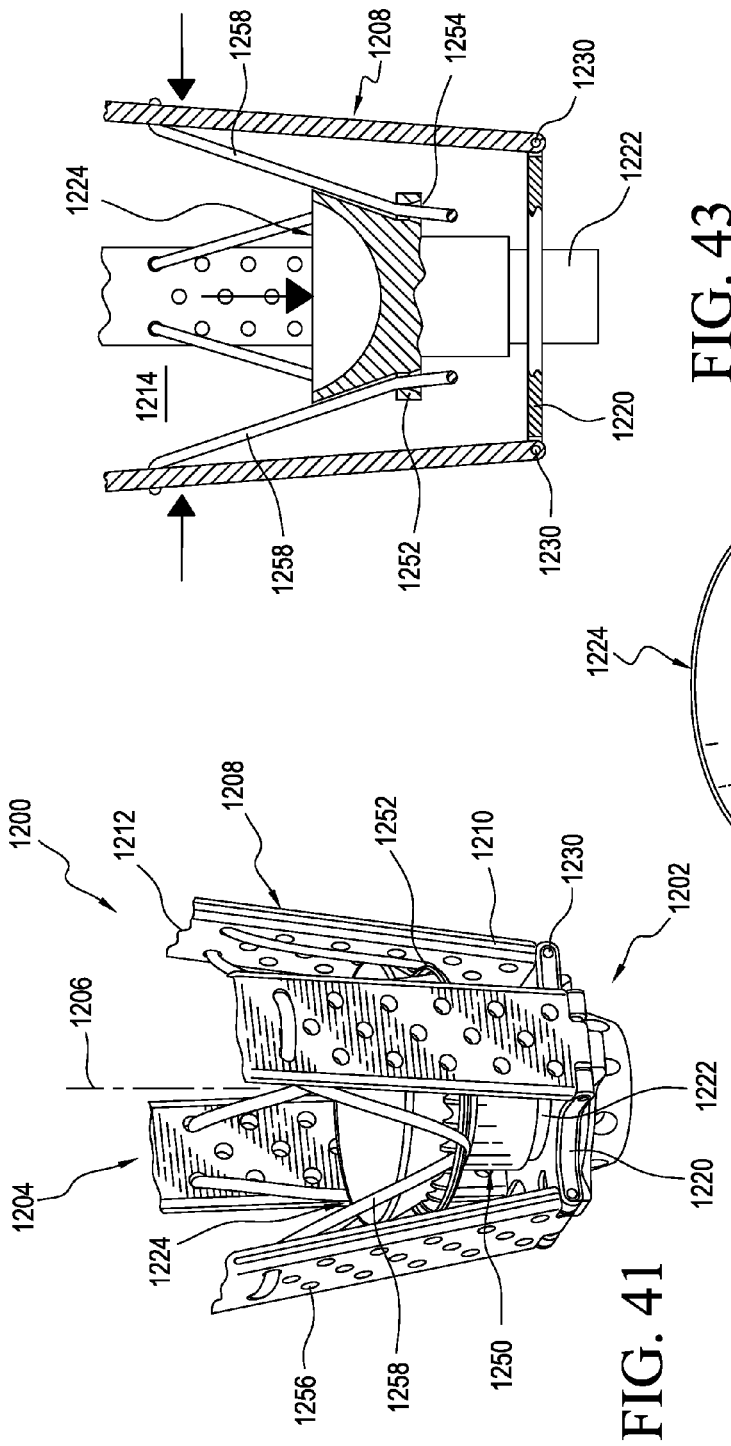

ADJUSTABLE SOCKET SYSTEM

TECHNICAL FIELD

The disclosure relates to an adjustable socket system for a residual limb.

BACKGROUND

A typical prosthetic leg and foot includes a socket, pylon, and foot. A socket is commonly referred to as the portion of a prosthesis that fits around and envelops a residual limb or stump, and to which prosthetic components, such as a foot, are attached. When providing a socket to an amputee, it is essential to properly fit the socket and align various parts of the prosthesis to the amputee. Fitting and alignment of the socket and the parts are difficult tasks to perform, and require extensive knowledge, training and skill for the prosthetist.

Typically, sockets for definitive prostheses are customized for a residual limb of a user. According to one method, the sockets are formed over a model of the stump, such as one formed by plaster-of-Paris, to be used to distribute forces between the socket and the stump in a comfortable way to the amputee. In another method, the socket may be obtained from computer aided design by modeling the shape of the stump, and subsequently forming a model. Once the model is obtained in either of these methods, a socket is formed over the model by using fabric and liquid plastic resin to obtain a definitive rigid socket customized to a limb.

Proper fitting of a socket to the stump is critical to the success of the prosthesis. The socket must fit closely to the stump to provide a firm connection and support, but must also be sufficiently loose to allow for circulation. In combination with proper fitting, the socket must transfer loads from the residual limb to the ground in a comfortable manner.

Most prosthetic sockets are permanently formed to a customized shape that is static, meaning the socket does not account for shape and volume fluctuations of the residual limb. When there are shape and volume fluctuations, the fitting of the socket is impeded, with these sockets causing discomfort, pain and soft tissue breakdown of the stump. Conventional sockets tend to be bulky and cumbersome to wear, and may be difficult to don making the residual limb uncomfortable when worn.

As to methods of attaching the socket to the residual limb, conventional sockets rely on different mechanisms such as negative pressure or a friction or tension based interface. Conventional sockets may have poor force distribution on the residual limb causing a concentration of pressure on a certain area of the stump. This poor distribution of pressure causes pain, discomfort, and tissue breakdown. Conventional sockets generally are not breathable which results in undesirable temperature and humidity within the socket.

For certain types of amputations such as disarticulation amputations where the limb is separated at a joint, it is difficult to create sockets which are not bulky and provide use of the natural anatomy. Conventional sockets for disarticulation amputations use a rigid socket which requires that the opening for the socket be larger than the joint to allow for donning and doffing. The rigid sockets generally have a general uniform shape which receives a large portion of the residual limb and the space between the residual limb and the interior of the rigid socket wall is filled in with a soft or cushioning material.

There is a need for an adjustable prosthetic socket that accommodates shape and volume fluctuations of the residual limb and comfortably transfers loads from the residual limb to the ground.

SUMMARY

The disclosure describes various embodiments of an adjustable socket system that is adapted to receive and fit a range of sizes of a residual limb, and accommodate volume and shape fluctuations of the residual limb. From its versatility in fitting and adjustment, the adjustable socket system can decrease pain, discomfort and soft tissue breakdown over known sockets static in size and shape.

Embodiments described can include an adjustable socket system having a distal portion and proximal portion. An axis extends between the distal and proximal portions. A plurality of struts are connected to the distal portion and distributed circumferentially about the axis. The struts at least in part define a receiving volume adapted to receive a residual limb and are movable between an expanded configuration in which at least some of the struts are moved radially outward relative to the axis to loosen the fit of the adjustable system, and a closed configuration in which at least some of the struts are moved radially inward relative to the axis to tighten the fit of the adjustable socket system. A tightening system is operatively connected to the struts and arranged to tighten and loosen the fit of the adjustable socket system on one or more areas of the residual limb. The tightening system can be manually or automatically operable.

According to a variation, the tightening system is arranged to automatically loosen and tighten the fit of the adjustable socket system when it is loaded and unloaded by a user. For instance, when the adjustable socket system is not in use, the struts can assume the expanded configuration, allowing a residual limb to be easily inserted into and removed from the receiving volume. When the residual limb is inserted into the receiving volume a distal end of the residual limb applies a load or pressure to a distal support of the tightening system, the tightening system automatically moves the struts toward the closed configuration, tightening the fit of the adjustable socket system on the residual limb in proportion to the load or pressure applied to the distal support.

The tightening system can thus advantageously permit the adjustable socket system to "relax" and be looser when the user is inactive (e.g., sitting or lying down) and become tighter when walking, and become very tight during sports. It also permits the adjustable socket system to tighten or clamp onto the residual limb during stance and loosen during swing, thus optimally using cyclic loading to best load or compress on the residual limb.

According to a variation, the tightening system is arranged to control the proportion of load or compression imparted by the struts to different areas of the residual limb, helping to create an improved fit between the adjustable socket system and the residual limb. For instance, insufficient compression or loading distally can create pistoning (e.g., excessive movement of the adjustable socket system up and down vertically relative to the residual limb). If there is too much loading distally, then it can be painful for the user of the system. If the proximal aspect of the system is too tight, then the residual limb can be forced in an upward direction out of the receiving volume, effectively stretching the residual limb, which can be uncomfortable and dangerous for the user. If the proximal aspect of the system is too loose, the distal aspect of the system can take too much load.

By controlling or fine-tuning the proportion of the distal compression and proximal compression, the tightening system can improve control and suspension.

Additional features and advantages of embodiments of the present disclosure will be set forth in the description that follows, and in part will be obvious from the description, or may be learned by the practice of such exemplary embodiments. These and other features will become more fully apparent from the following description and appended claims, or may be learned by the practice of such exemplary embodiments as set forth hereinafter.

BRIEF DESCRIPTION OF THE DRAWINGS

These and other features, aspects, and advantages of the present disclosure will become better understood regarding the following description, appended claims, and accompanying drawings.

FIG. 1 is an isometric view of an adjustable socket system according to an embodiment.

FIG. 2 is an isometric view of an adjustable socket system according to another embodiment.

FIG. 3 is an isometric view of an adjustable socket system according to another embodiment.

FIG. 4 is a top view of the adjustable socket system in FIG. 3.

FIG. 5 is a top view of the adjustable socket system in FIG. 3 in another position.

FIG. 6 is an isometric view of an adjustable socket system including a tightening system according to an embodiment.

FIG. 7 is a cross-sectional view of an adjustable socket system including a tightening system according to another embodiment.

FIG. 8 is a partial cross-sectional view of an adjustable socket system including a tightening system according to another embodiment.

FIG. 9 is a side view of an adjustable socket system including a tightening system according to another embodiment.

FIG. 10 is a side view of the adjustable socket system in FIG. 9 in another position.

FIG. 11 is a side view of an adjustable socket system including a tightening system according to another embodiment.

FIG. 12 is a side view of the adjustable socket system in FIG. 11 in another position.

FIG. 13 is a side view of an adjustable socket system including a tightening system according to another embodiment.

FIG. 14 is a side view of the adjustable socket system in FIG. 13 in another position.

FIG. 15 is an isometric view of an adjustable socket system including a tightening system according to another embodiment.

FIG. 19 is a cross-sectional view of an adjustable socket system including a tightening system according to another embodiment.

FIG. 20 is another cross-sectional view of the adjustable socket system in FIG. 19 in another position.

FIG. 21 is an isometric view of an adjustable socket system including a tightening system according to another embodiment.

FIG. 22 is a detailed view of the adjustable socket system in FIG. 21.

FIG. 23 is an isometric view of an adjustable socket system including a tightening system according to another embodiment.

FIG. 24 is another isometric view of the adjustable socket system in FIG. 23 in another position.

FIG. 25 is an isometric view of an adjustable socket system including a tightening system according to another embodiment.

FIG. 26 is an isometric view of an adjustable socket system including a tightening system according to another embodiment.

FIG. 27 is a schematic view of an adjustable socket system including a tightening system according to another embodiment.

FIG. 28 is a schematic view of an adjustable socket system including a tightening system according to another embodiment.

FIG. 29 is a schematic view of a tightening system according to another embodiment.

FIG. 30 is a schematic view of a tightening system according to another embodiment.

FIG. 31 is a schematic view of a tightening system according to another embodiment.

FIG. 32 is a schematic view of a tightening system according to another embodiment.

FIG. 33 is a cross section view of an adjustable socket system including a tightening system according to another embodiment.

FIG. 34 is the tightening system in FIG. 33.

FIG. 37 is a side view of an adjustable socket system including a tightening system according to another embodiment.

FIG. 38 is another side view of the adjustable socket system in FIG. 37.

FIG. 39 is a side perspective view of an adjustable socket system including a tightening system according to another embodiment.

FIG. 40 is a partial side view of the adjustable socket system in FIG. 39.

FIG. 41 is a side perspective view of an adjustable socket system including a tightening system according to another embodiment.

FIG. 42 is a bottom perspective of the distal support in FIG. 41.

FIG. 43 is a partial cross section view of the adjustable socket system in FIG. 41.

DETAILED DESCRIPTION OF VARIOUS EMBODIMENTS

Figure 18:
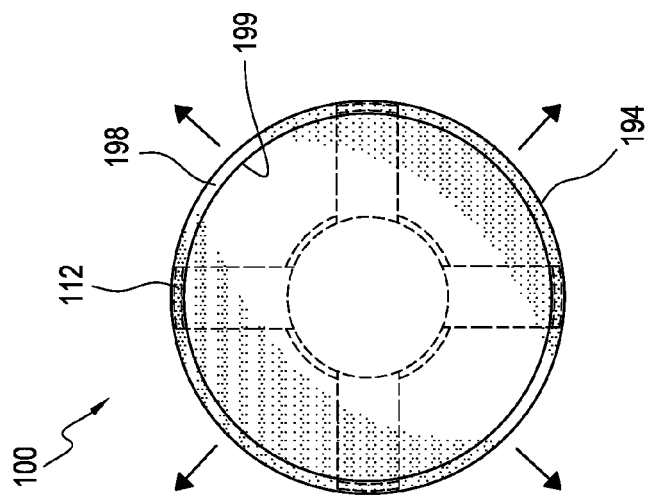
FIG. 18 is a top view of the adjustable socket system in FIG. 16 in another position.

A better understanding of different embodiments of the disclosure may be had from the following description read in conjunction with the accompanying drawings in which like reference characters refer to like elements.

While the disclosure is susceptible to various modifications and alternative constructions, certain illustrative embodiments are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

For further ease of understanding the embodiments of a prosthetic system as disclosed herein, a description of a few terms is necessary. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the prosthetic system. The term "rigid" is intended to denote that an element of the device is generally devoid of flexibility. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of members that provide support and are free-standing; however, such members may have some degree of flexibility or resiliency.

Some of the components described herein share similarities to components in U.S. Pat. Nos. 9,050,202; 8,795,385; 7,867,286; and 7,488,349 and pending U.S. application Ser. No. 14/704,572, incorporated herein by reference and belonging to the assignee of this disclosure.

FIG. 1 shows an embodiment of a prosthetic system comprising an adjustable socket system 100 that is adapted to receive and fit a range of sizes of a residual limb, as well as to accommodate volume and shape fluctuations of a residual limb. From its versatility in fitting and adjustment, the adjustable socket system can decrease pain, discomfort and soft tissue breakdown over known sockets that are static in size and shape. Moreover, the adjustability of the socket provides an off-the-shelf socket system that takes much of the guesswork out of making a socket and provides an instant solution when urgency may be required to provide an amputee with a socket. It will be appreciated that the system 100 may be adapted to a variety of different types of amputations, whether configured for the leg or arm.

The system 100 includes a distal portion 102, a proximal portion 104, and an axis 106 extending between the distal portion 102 and the proximal portion 104. The distal portion 102 is shown having a cup-like configuration but can have any suitable configuration. For instance, the distal portion can include a base connector adapted to connect to prosthetic components, such as an artificial foot or pylon.

A plurality of struts 108 having an elongated configuration are distributed circumferentially about the axis 106. Each of the struts 108 can include a distal end 110 connected to the distal portion 102 and a proximal free end 112. The struts 108 generally extend between the distal portion 102 and the proximal portion 104. The struts 108 can exhibit any suitable shape and/or size. For instance, at least one of the struts 108 can include parts extending in different directions along the outer surface of the residual limb, helping to distribute pressure from the struts 108 on the residual limb over a greater area. In other embodiments, the struts 108 can be adjustable or extendible in length. For instance, one or more of the struts 108 can include a telescoping mechanism that can adjust strut length or width. In other embodiments, the struts 108 can be available in different lengths and/or sizes that can be selectively attached to the distal portion 102 to adjust the length or size of the struts 108.

The struts 108 at least in part define a receiving volume 114 adapted to receive a residual limb. It will be appreciated that the configuration and distribution of the struts 108 about the axis 106 can be adjusted or selected based on the needs of the user for structural stability and/or to accommodate the underlying anatomy and physiology of the residual limb. At least some of the struts 108 are radially adjustable relative to the axis 106 to vary the receiving volume 114. The struts 108 or the system 100 is movable between an expanded configuration and a closed configuration. In the expanded configuration, at least some of the struts are moved or forced radially outward relative to the axis 106, increasing the receiving volume 114 or increasing a circumference of the system 100. This loosens the fit of the system 100 on a residual limb inserted in the receiving volume 114 or decreases the loading on the residual limb from the system 100. In the closed configuration, at least some of the struts 108 are moved or forced radially inward relative to the expanded configuration, decreasing the receiving volume 114 or decreasing a circumference of the system 100. This tightens the fit of the system 100 on the residual limb or increases the loading on the residual limb from the system 100. It will be appreciated that movement of one or more portions of a strut can move the struts 108 between the expanded and closed configurations.

According to a variation, at least one of the struts 108 can have a non-articulating configuration. For instance, the distal end 110 of one of the struts 108 can be rigidly connected to the distal portion 102 and the strut 108 can be adapted to bend or flex between the distal end 110 and the proximal end 112 to adjust or vary the receiving volume 114. This arrangement advantageously allows the system 100 to better accommodate the underlying anatomy and physiology of the residual limb, providing an improved fit between the system 100 and a residual limb in the receiving volume 114. In other embodiments, at least one of the struts 108 is adapted to pivot or articulate about a connection point relative to the axis 106.

One or more portions of the struts 108 can be at least in part rigid or semi-rigid, helping to provide support to the residual limb and/or stabilization of the system 100. The struts 108 can be of multi-durometer construction. For instance, the distal portion of the struts 108 can be semi-rigid and the proximal portion of the struts 108 can be rigid. This can allow the struts 108 to more easily expand or flex in response to volume fluctuations of the distal end of the residual limb. In an embodiment, the struts 108 can be contoured to generally correspond to an outer surface of the user's residual limb, which, in turn, creates a more comfortable fit. This can also improve cosmesis. For instance, a contour of one or more of the struts 108 can be adapted to make the system 100 less visible under trousers or other articles of clothing.

The system 100 can define pressure release regions adapted to allow for tissue displacement if the struts apply significant force to the tissues of the residual limb. The release regions may be in openings, recesses, soft elastically deformable material, or stiff material having regions that are elastically deformable. For instance, pressure release regions can include gaps 116 are defined between the struts 108. The gaps 116 can allow soft issue of the residual limb to bulge out between the struts 108, relieving pressure if needed and increasing user comfort. The gaps 116 can also provide ventilation to the system 100. Further, the gaps 116 can allow the struts 108 to be radially positioned closer to bone of the residual limb and may improve control of the system 100.

According to a variation, the distal portion 102 of the system 100 can include a distal support 118 as shown in FIG. 2. The distal support 118 is adapted to receive and support a distal end of the residual limb inserted in the receiving volume 114. The distal support 118 axially supports the residual limb to help prevent the distal end of the residual limb from "bottoming out" or displacing vertically to a base or other component below the distal support 118, which could negatively impact the distal end of the residual limb and potentially injure the user. The distal support 118 can be flexible such that it substantially conforms to the shape of the distal end of the residual limb.

The distal support 118 can have any shape but is shown having a cup-like configuration. The distal support 118 has a bottom portion and one or more side portions 120 arranged to extend up and around the distal end of the residual limb, providing protection and support to the distal end of the residual limb. The distal support 118 can be formed from an elastomeric material such as silicone or rubber. The distal support 118 can be a knitted, woven, or netted structure. The distal support 118 can be generally non-elastic in the axial direction such that when tension is applied to it, the distal support 118 can transfer load to the residual limb. The distal support 118 can provide a cushion and/or distribution of pressure at the distal end of the residual limb. As discussed in more detail below, the amount of pressure exerted on the residual limb by the distal support 118 can be adjustable and/or tensioned differently or independently of the struts 108.

According to a variation, the system 100 includes a plurality of petal members 124 operatively connected to the struts 108. One or more portions of the petal members 124 are arranged to move radially inward and/or outward relative to the axis 106, which, in turn, varies the receiving volume 114. The petal members 124 are situated radially inside of the struts 108 and extend along a length of the struts 108. In an embodiment, the petal members 124 define an inner surface 122 of the system 100 such that the petal members 124 form the interface between a residual limb and the system 100. This can help reduce the need of a separate liner and distribute pressure from the struts 108 to the residual limb, which, in turn, helps reduce the likelihood of the user feeling the struts 108 as points of pressure, improving user comfort. It also forms a larger contact surface between the residual limb and the system 100, providing a more secure coupling between the residual limb and the system 100.

As seen in FIG. 4, the petal members 124 are arranged in an overlapping configuration. For instance, each petal member 124 can include a leading edge 126 adapted to extend beyond a trailing edge 128 of an adjacent ones of the petal members 124. As such, there are none or almost no gaps or spaces present between adjacent ones of the petal members 124. This allows the petal members 124 to substantially enclose the residual limb within the system 100, which, in turn, prevents or limits soft tissue of the residual limb from bulging out between the struts 108. The leading and/or trailing edges 126, 128 are shown generally linear but can be arcuate, curvilinear, combinations thereof, or any other suitable configuration. The leading edge 126 and the trailing edge 128 can be the same or different.

As discussed above, one or more of the struts 108 are radially adjustable relative to the axis 106 to vary the receiving volume 114. When the struts 108 are moved radially inward, as seen in FIG. 5, the struts 108 move the petal members 124 radially inward toward the axis 106, decreasing the receiving volume 114. As the petal members 124 come together, the leading edges 126 slide or move a greater distance beyond the trailing edges 128 of the adjacent petal members 124. In an embodiment, the petal members 124 can come together to effectively become a single body forming a generally continuous inner surface area to interface with the residual limb. When the struts 108 are moved radially outward, the struts 108 move the petal members 124 radially outward from the axis 106, increasing the receiving volume 114. This allows the residual limb to be more easily inserted into and or removed from the system 100, facilitating donning and doffing the system 100. In an embodiment, the system 100 can include at least two struts 108 and at least two petal embers 124.

In an embodiment, the leading edges 126 and/or the trailing edges 128 can be adapted to form a seal with adjacent petal members 124 so that when the user places weight upon the system 100, the overlapping petal members 124 can in part create a substantially air-tight seal, allowing vacuum suspension of the system 100 on the residual limb.

One or more of the leading edges 126 can be rounded or rolled, helping it to more easily slide or move over the adjacent petal member 124. The distance the leading edge 126 overlaps the adjacent petal member 124 can vary between proximal and distal ends of the petal members 124. Optionally, at least one of the leading edges 126 or the trailing edges 128 can be chamfered or feathered. This can help prevent pressure points from the edges 126, 128 on the residual limb, providing a more comfortable fit. The leading edges 126 or the trailing edges 128 can be made of a softer durometer material than other portions of the petal members 124. For instance, one or more of the edges 126, 128 can comprise a flexible portion overmolded onto a body of the petal members 124. A distal portion of the petal members 124 can be thinner with a lower coefficient of friction than a proximal portion of the petal members 124, helping the petal members 124 to more easily slide or move over one another.

The petal members 124 can exhibit any suitable shape and/or configuration. The petal members 124 can be generally rectangular or trapezoidal. The petal members 124 can be generally leaf-shaped. The petal members 124 can have a shape that is preformed or customizable to an individual user. The petal members 124 can be shaped or contoured to generally correspond to the shape of a portion of the residual limb. An inner surface of one or more of the petal members 124 can have a resilient configuration, helping the petal members 124 to better fit the residual limb.

In an embodiment, the petal members 124 can be separate from and attached to the struts 108 via adhesives, mechanical fasteners, or any other suitable attachment method. In other embodiments, the petal members 124 and the struts 108 can be integrally formed in one piece. For example, one or more of the petal members 124 can be overmolded on the struts 108. The petal members 124 may or may not be attached to the struts 108.

The petal members 124 can have a multi-durometer configuration. In an embodiment, the proximal portion of the petal members 124 can be formed of a soft, compliant, conforming material arranged to follow the contour of the residual limb. The petal members 124 can include regions of softer durometer materials contained within larger areas of firmed durometer materials. The proximal portion of the petal members 124 can have a greater stiffness than a stiffness of the distal portion of the petal members 124. The petal members 124 can be formed of a flexible material, such as a polymeric material. The petal members 124 can be formed of a breathable material and situated directly next to the user's skin.

At least one of the petal members 124 can define one or more slots or cuts. For example, the petal members 124 can define a plurality of slots in a targeted region to increase flexibility or conformity of the petal member 124 within the targeted region. The slots or cuts can extend axially, circumferentially, and/or can exhibit any suitable size, shape, or length.

Embodiments of the adjustable socket system include a tightening system for tightening and loosening the fit of the adjustable socket system onto the user's residual limb. Embodiments of the tightening system can stabilize the struts or other structural components, contributing to the overall structural integrity of the adjustable socket system. The tightening system can provide adjustability to the adjustable socket system. Adjustments provided by the tightening system may include adjustments to the circumference of the adjustable socket system, or more particularly to the receiving volume defined by the struts. According to a variation, the tightening system can adjust tension or compression imparted to the struts even in the absence of noticeable change in the receiving volume. The tightening system can be manually or automatically operable.

Some embodiments of the tightening system can control a proportion compression imparted by the struts to different areas of the residual limb, helping to create an improved fit between the adjustable socket system and the residual limb. For instance, insufficient loading distally can create pistoning (e.g., excessive movement of the adjustable socket system up and down vertically relative to the residual limb). If there is too much loading distally, then it can be painful for the user of the system. If the proximal aspect of the system is too tight, then the residual limb can be forced in an upward direction out of the receiving volume, effectively stretching the residual limb, which can be uncomfortable and dangerous for the user. If the proximal aspect of the system is too loose, the distal aspect of the system can take too much load. By controlling or fine-tuning the proportion of the distal compression and proximal compression, the tightening system can improve control and suspension.

Some embodiments of the tightening system can control the fit of the adjustable socket system in different parts. Some embodiments of the tightening system can tighten and loosen the overall fit of the adjustable socket system but with a local control system so that the one part of the system can be tightened and loosened proportionally with respect to another portion of the system. In other embodiments, the tightening system can differentially control the fit of the adjustable socket system in different parts. In other embodiments, the tightening system can automatically tighten or loosen the adjustable socket system in response to loading and unloading of the system.

Different embodiments of the tightening system are shown in FIGS. 6-22. It will be appreciated that the tightening system embodiments described herein can be used alone or in combination with one or more features included in other embodiments of the present disclosure.

As shown in the example in FIG. 6, a tightening system 130 can include a tubular member 132 selectively positionable along a length of the struts 108 and arranged to adjust the fit of the system 100 on a residual limb. The tubular member 132 can define a continuous circumference. The tubular member 132 can be a sleeve 132 having a body portion 134 with open upper and lower ends 136, 138, and a central opening 137. The central opening 137 of the sleeve 132 defines an inner surface 139 for securing over an outer surface of the struts 108. The body portion 134 can have a circular or elliptical configuration.

The inner surface 139 can engage and frictionally secure against the outer surface of the struts 108. The body portion 134 may be formed from a fabric material and/or elastomer material. The body portion 134 can be radially stiff. The body portion 134 can be radially stretchable. The body portion 134 can generally resist elongation in the axial direction.

In use, the sleeve 132 is positioned on the distal portion 102 of the system 100 such that the struts 108 extend through the central opening 137 of the sleeve 132. The diameter of the central opening 137 is sized such that when the sleeve 132 is moved in a proximal direction along the outer surface of the struts 108, the inner surface 139 of the sleeve 132 imparts a compressive force on the struts 108, moving the struts 108 radially inward and tightening the fit of the system 100 on a residual limb.

The struts 108 can form a generally conical structure. As such, the amount of compression imparted to the struts 108 by the sleeve 132 can increase as the sleeve 132 is moved in a proximal direction along the length of the struts 108. The tightness of the system 100 on the residual limb can thus be controlled or varied by adjusting the axial position of the sleeve 132 along the struts 108. This advantageously allows a user to tighten the system 100 by positioning the sleeve 132 more closer to the proximal ends 112 of the struts 108 when the user is more active, and to loosen the system 100 by positioning the sleeve closer to the distal ends 100 of the struts 108 when the user is less active.

The sleeve 132 can also provide greater stability to the system 100. For instance, when the sleeve 132 is positioned near the proximal ends 112 of the struts 108, it can interconnect and stabilize the proximal ends 112 against undesired bending or expansion while allowing a length of the struts 108 below the sleeve 132 to bend or flex. This advantageously helps accommodate volume fluctuations of the distal end of the residual limb in the receiving volume 114. It will be appreciated that the sleeve 132 can form a large contact surface between the sleeve 132 and the struts 108, which, in turn, improves the connection between the system 100 and the residual limb.

According to a variation, the sleeve 132 can include a handle system including opposing handles 131 that a user can grasp to pull the sleeve 132 onto the struts 108. This can be done against resistance of the struts 108 or other components and the inner surface 139 of the sleeve 132. The handles 131 can be permanently attached to the sleeve 132 and storable thereon.

The handles 131 can be an add-on module and/or removable from the sleeve 132, allowing the handles 131 to be attached for donning and removed after donning the sleeve 132. In use, a user can grasp the handles 131 to pull the sleeve 132 onto the system 100 positioned on a residual limb. When the sleeve 132 is in a desired position, the user can remove the handles 131 from the sleeve 132. This advantageously facilitates placement of the tightening system 130 on the adjustable socket system 100.

FIG. 7 illustrates another embodiment of a tightening system 140 for tightening and loosening the adjustable socket system 100. The tightening system 140 includes a tubular member 144 selectively positionable on an outer surface of the struts 108 and arranged to adjust the fit of the system 100 on a residual limb. The tubular member 144 can define a continuous circumference. The tubular member 144 can comprise a ring member 144 defining a central opening 146. The ring member 144 can be formed of a rigid or substantially rigid material. The ring member 144 can be generally circular, generally elliptical, or any other suitable shape.

The struts 108 can extend through the central opening 146 of the ring member 144. The diameter of the central opening 146 is sized such that as the ring member 144 is forced in a proximal direction along the outer surface of the struts 108, the ring member 144 generally forces the struts 108 radially inward, reducing the receiving volume 114 and tightening the fit of the system 100 onto a residual limb. The amount of compression exerted on the residual limb can be increased as the ring member 144 is moved in the proximal direction along the struts. While one ring member is shown, in other embodiments, the tightening system 140 can include a plurality of ring members. For instance, the tightening system 140 may include a distal ring member arranged to be used and adjusted on an initial fitting of the system 100 and a proximal ring member arranged to be used and adjusted regularly by a user.

According to a variation, the ring member 144 may be spring loaded. For instance, a pair of spring members 148 may extend on opposite sides of the ring member 144 between the ring member 144 and a part of the distal portion 102. Each spring member 148 may exhibit a force constant or K-value. The spring members 148 can have the same or different K-values. If the K-value of each spring member 148 is generally the same, then the ring member 144 can generally center the struts 108 about the residual limb in the receiving space 114, which, in turn, causes the struts 108 to apply substantially the same pressure to a residual limb positioned in the receiving space 114. If the K-value of the spring members 148 is different, the ring member 144 applies uneven forces to the struts 108, which, in turn, causes the struts 108 to apply uneven pressure to the residual limb. For instance, the ring member 144 can generate more compression anteriorly on the residual limb as to posteriorly on the residual limb. This can also allow the ring member 144 to be tilted or oriented in a non-parallel position relative to the ground. It will be appreciated that in other embodiments, the tightening system 140 may include one, three, four, or any other suitable number of spring members.

According to a variation, the tightening system 140 may include a locking mechanism for selectively securing the ring member 144 in place on the struts 108 as seen in FIG. 8. For instance, one or more of the struts 108 can define one or more notches 141 for receiving one or more locking members 143 protruding radially inward from the inner diameter of the ring member 144. The notches 141 may exhibit any suitable shape. In an embodiment, the locking members 143 can comprise spring-loaded pegs that are selectively receivable in the notches 141 for holding the ring member 144 in place on the struts 108.

FIGS. 9 and 10 show a tightening system 150 for tightening and loosening the adjustable socket system 100 according to another embodiment. The tightening system 150 comprises a tubular member 152 selectively positionable on an outer surface of the struts 108 and arranged to adjust the fit of the system 100 on a residual limb. The tubular member 152 can define a continuous circumference. The tubular member 152 can comprise a sleeve 152 having a body portion 154 extending between a closed distal end 156 and an open proximal end 158. The sleeve 152 can be formed of an elastomeric material, a fabric material, combinations thereof, or any other suitable material. The sleeve 152 can be formed of a breathable material. The body portion 154 can be generally cylindrical or conical. The body portion 154 can define a substantially continuous inner surface. The body portion 154 can define an inner volume for receiving the system 100.

At least a portion of the body portion 154 is configured to roll onto itself and unroll to adjust compression applied to the struts 108 by the sleeve 152, which, in turn adjusts loading of the residual limb in the area of the sleeve 152 by the struts 108. The body portion 154 may include a constant thickness. The body portion 154 may include a tapered thickness from the distal end 156 toward the proximal end 158. The thickness of the body portion 154 can provide additional cushioning at the distal end of the system 100, and easier roll-on/off at the proximal end when the sleeve 152 is donned and doffed. The body portion 154 may exhibit different stiffness in different areas or zones. The body portion 154 may be elastically resilient. The body portion 154 can be radially stretchable.

In use, with the residual limb in the receiving space 114, the sleeve 152 is rolled up from the proximal end 158 toward the distal end 156, and placed over the distal portion 102 of the system 100 with the distal end 156 of the sleeve 152 positioned on the struts 108 as shown in FIG. 9. This allows the sleeve 152 to impart a first compressive force on the struts 108 toward the distal portion 102 of the system 100, tightening the fit of the system 100 on a distal part of the user's residual limb.

The sleeve 152 is then rolled back up or out over the struts 108 as shown in FIG. 10. With the sleeve 152 rolled out over the proximal ends 112 of the struts 108, the sleeve 152 imparts a second compressive force on the struts 108 in the proximal portion 104. This forces the proximal ends 112 of the struts 108 radially inward, which, in turn, tightens the fit of the system 100 onto a proximal part of the user's residual limb. The sleeve 152 rolled out over the proximal ends 112 of the struts 108 also helps stabilize the struts 108. The tightening system 150 can thus adjust the fit of the system 100 on different areas of the residual limb. In an embodiment, the sleeve 152 can be configured to exert a greater compressive force on the proximal portion 104 of the system 100 than the distal portion 102 or vice versa, proportionally tightening or loosening the system 100.

In addition, because the sleeve 152 is separate from the struts 108, the struts 108 can be moved or forced radially outward from the axis 106 before the sleeve 152 is positioned on the system 100, facilitating donning. The closed distal end 156 of the sleeve 152 creates a connection between the sleeve 152 and the distal portion 102 of the system 100 after the system 100 is donned on a residual limb and the sleeve 152 is secured on the system 100. This advantageously can assist a user with placement of the tightening system 150, improving ease of use. In an embodiment, properties of the body portion 154 can resiliently compress the sleeve 152 against the struts 108 in a radially inward direction.

According to a variation, the tightening system 150 includes a plurality of sleeves, each arranged to apply a different compression to the struts 108. For instance, a first sleeve can be configured to apply a lower compression for a first fit of the system 100 and a second sleeve can be configured to apply a higher compression for a second fit of the system 100, allowing the fit of the system 100 to be adjusted or customized based on user characteristics, activity levels, and/or other factors.

In an embodiment, the body portion 154 can have a length dimensioned so that when the sleeve 152 is rolled out over the struts 108, the body portion 154 extends axially beyond the proximal ends 112 of the struts 108. Optionally, the body portion 154 can have a length dimensioned so that when the sleeve 152 is rolled out over the struts 108 it extends axially beyond the proximal ends 112 of the struts 108 to form a brim part. The brim part can allow for proximal loading and more proximal stability of the system 100 on the residual limb. The brim part can also enable more even distribution of loading and consistent stability around the proximal end of the system 100.

In another embodiment of the tightening system of the disclosure of FIGS. 11 and 12, a tightening system 160 comprises a tubular member 162 positionable on the struts 108 and arranged to adjust the fit of the system 100 on a residual limb. The tubular member 162 can define a continuous circumference. The tubular member 162 may comprise a sleeve 162 having a body portion 164 with open upper and lower ends 166, 168, and an inner surface 169 for securing over an outer surface of the system 100 and/or the residual limb. For instance, the inner surface 169 can engage and frictionally secure against the outer surface of the struts 108 and residual limb. The body portion 164 can be formed of any of the materials previously described.

As shown, the body portion 164 can have an elongate configuration extending between the upper and lower ends 166, 168. The body portion 164 can form a circle or ellipse. At least a portion of the body portion 164 is arranged to be rolled onto itself. The body portion 164 can have a constant or variable thickness. The body portion 164 may be elastically resilient.

In use, the sleeve 162 is at least in part rolled up from the distal end 166 to the proximal end 168 on the residual limb proximal of the system 100 as shown in FIG. 11. The residual limb is then placed in the receiving space 114. The sleeve 162 is then rolled back down or out over the struts 108 as shown in FIG. 12. With the sleeve 162 rolled out over the outer surface of the struts 108, the sleeve 162 imparts a compressive force on the struts 108, which, in turn, forces the struts 108 radially inward. This increases loading of the residual limb in the area of the sleeve 162 by the struts 108 and tightens the fit of the system 100 on the residual limb. In an embodiment, the distance the sleeve 162 is rolled out over the struts 108 can be varied to adjust the compressive force imparted to the struts 108, which, in turn, adjusts the location and/or magnitude of loading on the residual limb by the system 100. The sleeve 162 also stabilizes the struts 108 on the residual limb.

Because the sleeve 162 is open ended, the position of the sleeve 162 relative to the struts 108 is freely adjustable. As such, the position of the sleeve 162 along the axis 106 can be varied to increase or decrease the contact surface area between the sleeve 162 and the system 100 and the sleeve 162 and the residual limb. It will be appreciated that the steps described above can be performed in different orders. For instance, the sleeve 162 can be positioned on the distal portion 102 of the system 100 before the residual limb is inserted in the receiving space 114.

In an embodiment, the sleeve 162 can be arranged to extend more than about 0.3 times, about 0.4, about 0.5 times, or about 0.6 times the length of the struts. As seen in FIG. 12, the sleeve 162 can be positioned on the residual limb to form a brim part extending in axial direction beyond the proximal ends 112 of the struts 108. The brim part can form a greater contact surface area between the sleeve 162 and the residual limb. The brim part can allow for proximal loading and more proximal stability of the system 100 on the residual limb. In an embodiment, the sleeve 162 can define an adjustable circumference. This allows a clinician or user to adjust the sleeve 162, decreasing the number of sizes and/or optimizing stability and comfort.

FIGS. 13 and 14 show another embodiment of a tightening system 170 including a tubular member 172 selectively positionable on the struts 108 and arranged to adjust the fit of the system 100 on a residual limb. The tubular member 172 can define a continuous circumference.

The tubular member 172 can be a sleeve 172 having a body portion 174 extending between a closed distal end 176 and an open proximal end 178. The sleeve 172 can be formed of any of the materials previously described. The body portion 174 can be generally cylindrical or conical. The body portion 174 can define an inner volume for receiving the system 100.

The sleeve 172 can include a brim part 179 attached to the body portion 174 and defining the proximal end 178 of the sleeve 172. The brim part 179 is arranged to move relative to the body portion 174 to adjust compression imparted to the struts 108 by the sleeve 172. For instance, the proximal end 178 of brim part 179 is arranged to be folded back onto the sleeve 172 from an original position and to be resiliently flipped or rolled back to the original position. The brim part 179 can be made from a same or different material than the body portion 174. The brim part 179 can be a soft member arranged to conform to the shape of the residual limb. The brim part 179 can have a symmetrical shape such as a cylindrical shape. The brim part 179 can have an asymmetrical shape. For instance, the brim part 179 can be arranged to extend a length along the posterior of the sleeve 172, increasing seated comfort for a user of the system 100.

In use, with the residual limb positioned in the receiving space 114, the sleeve 172 can be positioned on the distal portion 102 of the system 100 with the proximal end 178 of the brim part 179 folded back onto itself, imparting a first compression to the struts 108 in the distal portion 102. With the sleeve 172 positioned on the distal portion 102, the sleeve 172 forces the struts 108 in the distal portion 102 radially inward, increasing the load and tightening the fit of the system 100 in at least the distal portion 102 onto the residual limb.

The proximal end 178 of the brim part 179 can then be flipped or folded up over the proximal ends 112 of the struts 108 as shown in FIG. 14, imparting a second compression to the proximal ends 112 of the struts 108. With the sleeve 172 positioned on the struts 108 and the brim part 179 flipped up, the sleeve 172 forces the struts 108 in the proximal portion 104 radially inward, increasing the load and tightening the fit of the system 100 in the proximal portion 104 onto the residual limb. The tightening system 170 can thus adjust the fit of the system 100 on different areas of the residual limb. The tightening system 170 also interconnects and stabilizes the struts 108.

It will be appreciated that the steps described above can be performed in one or more different sequences. For instance, the sleeve 172 can be positioned on the distal portion 102 of the system 100 before the residual limb is inserted in the receiving space 114.

FIG. 15 shows another embodiment of a tightening system 180 including a tubular member 182 positioned on the struts 108 and arranged to adjust the fit of the system 100 on a residual limb. The tubular member 182 can define a continuous circumference. The tubular member 182 can include a sleeve 182 forming a brim part 184. The brim part 184 can be connected to the proximal end 112 of two or more of the struts 108. The brim part 184 can have open upper and lower ends 186, 188, an outer surface arranged to engage the struts, and an inner surface 181 arranged to provide an interface between the proximal portion 104 of the system 100 and the residual limb. The brim part 184 can be formed as a molded member, such as by injection molding. The brim part 184 can be formed of an elastomeric material or another suitable material.

The sleeve 182 is configured to apply tension and compression to the struts 108 to adjust the fit of the system 100. For instance, the brim part 184 can be manually expanded radially outward, forcing the proximal ends 112 of the struts 108 radially outward and loosening the fit of the system 100, and the properties or elasticity of the brim part 184 can force the struts 108 radially inward, tightening the fit of the system 100 onto the residual limb.

In an embodiment, a user can grip and stretch the brim part 184 radially outward to move the system 100 to the expanded configuration. With the system 100 in the expanded configuration, a user can position the residual limb in the receiving space 114, facilitating donning. To move the struts 108 to the closed configuration, the user can release the brim part 184 so that the properties or elasticity of the brim part 164 pull the struts 108 radially inward, increasing the load and tightening the fit of the system 100 onto the residual limb.

Because the brim part 184 is positioned between the struts 108 and the residual limb, the brim part 184 can distribute pressure from the struts 108 to the residual limb, providing a more even distribution of pressure from the system 100 on the residual limb. This helps improve the fit and feel of the system 100. Similar to other embodiments, the brim part 184 can also stabilize the proximal ends 112 of the struts 108 against undesired bending while allowing a length of the struts 108 below the brim part 184 to bend or flex.

The brim part 184 can be weight bearing (e.g., arranged to transfer load from the pelvis) or non-weight bearing. In other embodiments, the inner surface 181 of the brim part 184 can engage the outer surface of the struts 108. The number of struts 108 the brim part 184 is attached to can be varied, varying the fit and stability of the system 100. The brim part 184 can be ischial bearing or sub-ischial bearing. As noted above, embodiments of the tightening system can be used alone or in combination with other embodiments of the tightening system. For instance, the tightening system 180 can be used in combination with any of the previously described tightening systems.

Figure 17:
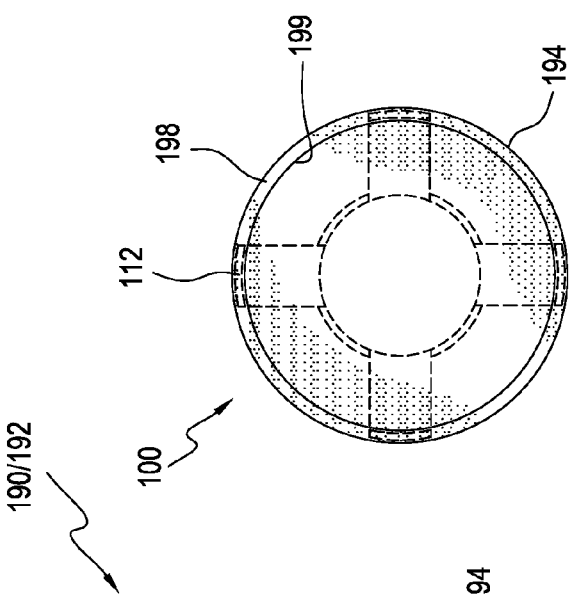
FIG. 17 is a top view of the adjustable socket system in FIG. 16.
Figure 16:
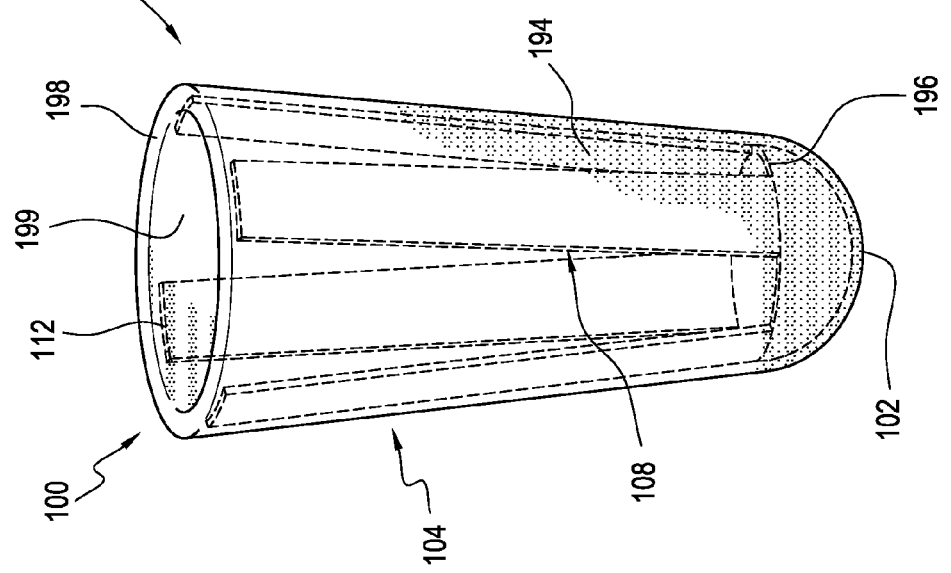
FIG. 16 is an isometric view of an adjustable socket system including a tightening system according to another embodiment.

FIGS. 16-18 show another embodiment of a tightening system 190 including a tubular member 192 positioned on the struts 108 and arranged to adjust the fit of the system 100 on a residual limb. The tubular member 192 can define a continuous circumference. The tubular member 192 can be a sleeve 192 integrated with the struts 108. The sleeve 192 has a body portion 194 extending between a distal end 196 and an open proximal end 198. The distal end 196 may be open or closed. The sleeve 192 can be formed of any of the materials previously described. The body portion 194 can be generally cylindrical or conical. The body portion 194 can have an inner surface 199 that at least in part defines the receiving volume 114 of the system 100. The body portion 194 can conform to the specific shape of the residual limb. The body portion 194 can rely on deformation to stretch and compress. At least a part of the body portion 194 can be formed of a polymeric material and/or an elastomeric material to allow for such deformation.

The struts 108 can be embedded within the body portion 194. The struts 108 can extend along an outer surface of the struts 108. In an embodiment, the body portion 194 can be separate from and attached to one or more of the struts 108 via adhesives, mechanical fasteners, or any other suitable attachment means. In other embodiments, the body portion 194 and the struts 108 can be integrally formed in one piece. For example, the body portion 194 can be overmolded to the struts 108.

As noted above, the inner surface 199 at least in part defines the receiving volume 114 such that the sleeve 192 forms an interface between the residual limb and the system 100. This advantageously reduces the likelihood of the user feeling the struts 108 as pressure points, increasing comfort. This also increases the contact surface area between the system 100 and the residual limb, creating a more secure fit between the residual limb and the system 100.

In an embodiment, the sleeve 192 is arranged to form an air-tight coupling or connection between the residual limb and the system 100, permitting vacuum and elevated suspension. The sleeve 192 can also help prevent tissue from bulging out of the system 100.

The sleeve 192 can include an outer textile layer and inner silicone layer or a reinforcement material embedded within a polymeric material. In an embodiment, the sleeve 192 may include a soft or low density polyethylene. In other embodiments, the sleeve 192 can include rigid sections and flexible sections positioned in strategic locations, allowing the sleeve 192 to provide targeted support and/or pressure relief. The sleeve can include a single layer or multiple layers. For instance, the sleeve 192 can include an inner layer arranged to be next to the user's skin and an outer layer.

Similar to the previous embodiment, the sleeve 192 is configured to apply tension and compression to the struts 108 to adjust the fit of the system 100. In use, a user can grip and stretch a proximal part of the body portion 194 radially outward to move the struts 108 to the expanded configuration as shown in FIG. 17, facilitating donning. To move the struts 108 to the closed configuration as shown in FIG. 18, the user can release the body portion 194 so that the properties or elasticity of the body portion 194 forces the struts 108 radially inward, increasing the load and tightening the fit of the system 100 on the residual limb 100. Forces applied by the body portion 194 on the struts 108 can be symmetrical or asymmetrical. For instance, the body portion 194 can apply a greater force along one side of the system 100 as compared to another.

Similar to the previous embodiment, the sleeve 192 helps distribute pressure from the struts 108 to the residual limb, improving the fit and feel of the system. Because the struts 108 are embedded or located within a thickness of the body portion 194, the sleeve 192 also stabilizes the struts 108 against undesired bending. Furthermore, the tightening system 190 can be used alone or in combination with previously described tightening systems. For instance, the tightening system 190 can be used in combination with the tightening system 160 to secure the system 100 on a residual limb.

Referring to FIGS. 19 and 20, the tightening system 190 can include at least one tensioning element arranged to help move the struts 108 between the expanded and closed configurations. For instance, a tensioning element 202 can be routed through or attached to the body portion 194. In an embodiment, the tensioning element 202 can include a first end 204 anchored to the sleeve 192 and a second free end 206 extending in a proximal direction beyond the sleeve 192. The tensioning element 202 can be arranged in a zig-zagging pattern. FIG. 19 shows the system 100 with the struts 108 in the expanded configuration. To move the struts 108 toward the closed configuration, a user can tension or pull the tensioning element 202 to shorten the length of the tensioning element 202 within or attached to the body portion 194, which, in turn, pulls the struts 108 closer together as seen in FIG. 20. The tensioning element 202 may be formed from any type of line, cord, strap, rope, string, wire, cable, or other suitable element.

According to a variation, the tightening system 190 can include a sleeve 192A having a plurality of sections 214 extending between the proximal and distal ends of the sleeve 192A as seen in FIGS. 21 and 22. The sections 214 can be circumferentially distributed about the sleeve 192A. For instance, the sections 214 can include a first section 214A opposite a second section 214B, and a third section 214V opposite a fourth section 214D. The sections 214 can have a corrugated or accordion-like configuration. The sections 214 are arranged to facilitate movement of the struts 108 between the expanded and closed configurations. In an embodiment, areas 216 of the sleeve 192A between the sections 214 can be rigid or semi-rigid. This allows the areas 216 to provide support to the residual limb and stabilization to the system 100 while the sections 214 provide stretchiness and flexibility to the sleeve 192A.

FIGS. 23-43 show embodiments of the adjustable socket system including tightening systems arranged to mechanically control or adjust the fit of the system on a residual limb. It will be appreciated that these systems can include many of the same or similar features as the embodiments in FIGS. 1-22. In addition, it will be appreciated that the mechanical tightening system embodiments can be used alone or in combination with the tightening systems previously described.

As shown in the example in FIGS. 23 and 24, an adjustable socket system 300 includes a distal portion 302, a proximal portion 304, and an axis 306 extending between the distal portion 302 and the proximal portion 304. The distal portion 302 can include a base 320 and a distal support 322. The distal support 322 is adapted to receive and support a distal end of the residual limb inserted in the receiving volume 314.

A plurality of struts 308 are connected to the distal portion 302 and generally extend between the distal portion 302 and the proximal portion 304. The struts 308 at least in part define a receiving volume 314 adapted to receive a residual limb. It will be appreciated that the struts 308 can be adjustable in length. For instance, one or more of the struts 308 can have a telescoping mechanism that can adjust strut length or width. In other embodiments, the struts 308 can be available in different lengths and/or sizes that can be selectively attached to the distal portion 302 to adjust the length or size of the struts 308.

At least some of the struts 308 are radially adjustable relative to the axis 306 to vary the receiving volume 314. The struts 308 can be movable between an expanded configuration in which at least some of the struts are moved radially outward relative to the axis 306 to loosen the fit (or decrease the load) of the system 300 on a residual limb, and a closed configuration in which at least some of the struts 308 are moved radially inward relative to the expanded configuration to tighten the fit (or increase the load) of the system 300 on the residual limb.

In an embodiment, each of the struts 308 are arranged to rotate relative to the base 320 via a pivot point 324 to vary the receiving volume 314. The pivot point 324 can comprise a hinge mechanism, a pinned connection, and/or any other suitable type of pivot connection. Each pivot point 324 can comprise a pin member pivotally connecting the strut 308 to the base 320. The pivot points 324 can be located at or near the base 320.

A tightening system 330 is arranged to move the struts 308 between the expanded and closed configurations. Optionally, the system 300 can include a biasing mechanism arranged to bias the struts 308 toward the expanded configuration. The tightening system 330 can comprise a threaded portion 332 defined on an outer surface of the base 320 and an actuating part 334 comprising a collar member 334 defining an internal threaded portion 335 attached to the threaded portion 332 of the base 320. When the collar member 334 is rotated relative to the base 320, the threaded connection between the collar member 334 and the base 320 moves the collar member 334 proximally or distally along the axis 306. The collar member 334 can include a rigid or semi-rigid material.

To move the struts 308 toward the closed configuration, a user or clinician can rotate the collar member 334 in a first direction relative to the base 320, which, in turn, moves the collar member 334 proximally or upward along the axis 306. As the collar member 334 moves proximally, an inner surface 336 of the collar member 334 can move upwardly along the outer surface of the struts 308, which, in turn, moves or rotates the struts 308 about the pivot points 324 toward the closed configuration, tightening the fit (or increasing the load) of the system 300 on a user's residual limb.

To move the struts 308 toward the expanded configuration, the user or clinician can rotate the collar member 334 in a second direction opposite the first direction, which, in turn, moves the collar member 334 distally or downward along the axis 306. As the collar member 334 moves distally, the inner surface 336 of the collar member 334 can move downwardly along the outer surface of the struts 308, which, in turn, allows the struts to move or rotate about the pivot points 324 back toward the expanded configuration, loosening the fit (or decreasing the load) of the system 300 on the user's residual limb. This advantageously allows a user or clinician to selectively rotate the collar member 334 relative to the base 320 to tighten and loosen the system 300. It will be appreciated that the range adjustment of the system 300 can be defined or varied at least in part by the thread angle, pitch, and/or lead of the threaded portions on the collar member 334 and base 320.

FIG. 25 illustrates another adjustable socket system 400 including a tightening system for controlling or adjusting the fit of the system 400. It will be appreciated that the system 400 can be similar to and can include many of the same or similar features as any of the other embodiments described herein. The system 400 includes a distal portion 402, a proximal portion 404, and an axis 406 extending between the distal and proximal portions 402, 404. The distal portion 402 can exhibit any suitable configuration. The distal portion 402 includes a base 420 forming a limb receiving portion or seat adapted to receive a distal end portion of a residual limb. A base connector 422 is secured to a bottom portion of the base 420, and is adapted to connect to prosthetic components.

A plurality of struts 408 are connected to the distal portion 402 and generally extend between the distal portion 402 and the proximal portion 404. At least some of the struts 408 are radially adjustable relative to the axis 406 to vary the receiving volume 414. The struts 408 can be movable between an expanded configuration in which at least some of the struts are moved radially outward to loosen the fit of the system 400 on a residual limb, and a closed configuration in which at least some of the struts 408 are moved radially inward to tighten the fit of the system 400 on the residual limb.

The struts 408 can be generally linear or curved. The struts 408 can be contoured to correspond to the contour of the residual limb. The struts 408 can include one or more rod members 428. Each strut 408 can include a pair of rod members 428. Optionally, one or more of the rod members 428 can have a telescoping mechanism, allowing the length of the strut 408 to adapt to residual limbs of different lengths. The struts 408 can include multiple parts.

The struts 408 can include one or more support members 430 at or near a proximal portion of the struts 408. In an embodiment, the support members 430 can extend along a length of the rod members 428. The support members 430 can have any suitable shape but are shown shaped to generally correspond to a portion of a residual limb of a user. The support members 430 can be overmolded on the rod members 428. The support members 430 can be formed of a plastic material, a rubber material, or any other suitable material. Optionally, an inner surface of the support members 430 can have a resilient configuration such that the inner surface generally conforms to the residual limb.

The support members 430 define an interface between the residual limb and the system 400. The support members 430 can have a width arranged to form a larger contact surface between the residual limb and the system 400, providing a more secure fit. This also helps distribute pressure or loads from the struts 408 to the residual limb. This has the effect of reducing the likelihood of the user feeling the struts 408 as pressure points, improving comfort. The width of the support members 430 can vary. The width of the support members 430 can generally taper in a distal direction to help provide a better fit.

A tightening system 432 is arranged to move the one or more portions of the struts 408 between the closed and expanded configurations and/or to stabilize the struts 408. The tightening system 432 includes a plurality of tensioning elements 436 rotatably linked to a plurality of tensioning control mechanisms 434 and operatively connected to the struts 408. The tensioning elements 436 may be formed from any type of line, cord, strap, rope, string, wire, cable, or other suitable element. At least one of tensioning control mechanisms 434 can have rotational increments, allowing the tension in the at least one tensioning element 436 to be incrementally increased or decreased. It is advantageously simple for the user to quickly adjust the tension in the system 400. Other exemplary tensioning control systems can be found in U.S. patent application Ser. No. 13/930,053 and U.S. Pat. No. 8,795,385, each of which is incorporated by reference in its entirety.

When at least one of the tensioning control mechanisms 434 is rotated in a first direction, a corresponding tensioning element 436 is drawn into the tensioning control mechanism 434, increasing tension in the tensioning element 436. This causes the struts 408 in one or more areas of the system 400 to move toward the closed configuration, tightening the fit of the system 400. When at least one of the tensioning control mechanisms 434 is rotated in a second direction opposite the first direction, a corresponding tensioning element 436 exits the tensioning control mechanism 434, decreasing tension in the tensioning element 436. This allows the struts in one or more areas of the system 400 to move toward the expanded configuration, loosening the fit of the system 400.

In an embodiment, the tightening system 432 tensions the struts 408 to apply equal or substantially equal pressure to the residual limb, helping to limit pressure points from forming on different areas of the residual limb. Pressure points on the residual limb can be problematic in that the pressure points cause irritation, pain, and discomfort to the user. For instance, each tensioning control mechanism 434 can be operatively connected to all or substantially all of the tensioning elements 436 such that operation of one of the tensioning control mechanisms 434 tensions all of the tensioning elements 436 at a same or substantially same level.

The tensioning control mechanisms 434 can be located anywhere on the system 400 but are shown located on the base 420 of the distal portion 402. In an embodiment, at least one of the tensioning elements 436 can be fed or passed through an interior space of the rod members 428. From the rod members 428, the tensioning element 436 can extend to the support members 430 where it passes through guides 438 formed on the support members 430 and between the support members 430. The tightening system 432 can tension the struts 408 more toward the proximal portion 404 than the distal portion 402, controlling the fit of the system 400.

According to a variation, the tightening system 432 can proportionally control the fit of the system 400 on a residual limb. For instance, the tensioning control mechanisms 434 include a first tensioning element 436A rotatably linked to a first tensioning control mechanism 434A operatively connected to a first area of the system 400 and a second tensioning element 436B rotatably linked to a second control mechanism 434B operatively connected to a second area of the system 400. As such, the position and/or force applied to the struts 408 in the first area of the system 400 can be controlled by tensioning the first tensioning element 436A. The position and/or force applied to the struts 408 in the second area of the system 400 can be controlled by tensioning the second tensioning element 436B.

This advantageously allows the fit of the system 400 in the first area to be adjusted and/or controlled independently of the second area of the system 400. The first area can be an anterior side and the second area can be a posterior side or vice versa. The first area can be a medial side and the second area can be a lateral side or vice versa.

FIG. 26 illustrates another adjustable socket system 500 including a tightening system for controlling or adjusting the fit of the system 500. The system 500 can be similar to and can include many of the same or similar features as any of the other embodiments described herein. The system 500 includes a distal portion 502, a proximal portion 504, and a plurality of struts 508 connected to the distal portion 502 and generally extending between the distal portion 502 and the proximal portion 504. The distal portion 502 includes a base 520 forming a limb receiving portion. A base connector 522 is secured to a bottom portion of the base 420, and is adapted to connect to prosthetic components.

One or more portions of the struts 508 can move radially inward and/or outward to vary a receiving volume 514 adapted to receive a residual limb. For instance, the struts 508 can be movable between an expanded configuration in which at least some of the struts 508 are moved radially outward to loosen the fit of the system 500 on a residual limb inserted in the receiving volume 514, and a closed configuration in which at least some of the struts 508 are moved radially inward to tighten the fit of the system 500 on the residual limb.

A tightening system 530 is operatively coupled to the struts 508 and arranged to move the struts 508 between the expanded configuration and the closed configuration. The tightening system 530 can include at least one tensioning control mechanism 532 and at least one tensioning element 534. The at least one tensioning element 534 is rotatably linked to the at least one tensioning control mechanism 532 and connecting two or more of the struts 508. When the at least one tensioning element 534 rotates in a first direction, tension in the at least one tensioning element 534 increases, which, in turn, moves the struts 508 toward the closed configuration and tightens the system 500. When the at least one tensioning element 534 rotates in a second direction opposite the first direction, tension in the at least one tension element 534 decreases, allowing the struts 508 to move toward the expanded configuration and loosening the fit of the system 500.

The tightening system 530 can be operatively coupled to a distal support 516 adapted to receive and support a distal end of the residual limb inserted in the receiving volume 514. The distal support 516 can be positioned proximal of the base 520 such that it can be tensioned by the tightening system 530. In an embodiment, tension applied to the distal support 516 by the tightening system 530 can create axial pressure on the residual limb, helping to support a user's weight. The applied tension can also create radial pressure on the distal end of the residual limb, helping to stabilize the residual limb. Thus, through adjustment of the tightening system 530 the fit of the system 500 and the level of load or pressure applied by the distal support 516 can be controlled and/or adjusted.

This is advantageous because if the axial pressure applied to the residual limb by the distal support 516 is insufficient, the residual limb can painfully bottom out. Further, radial pressure applied to the residual limb by the struts 508 must be sufficient to secure the residual limb within the system 500 and limit pistoning but if it is too high the struts 508 may strangle the residual limb, causing discomfort and/or cutting off circulation to the residual limb. By adjusting and/or controlling the load or pressure applied to the distal end of the residual limb, the tightening system 530 can provide both a secure and comfortable fit.

Optionally, the distal support 516 can be tensioned differently or independently of the tensioning of the struts 508. For instance, the tightening system 530 can include a tensioning control mechanism as described below including a first control part operatively connected to the distal support 516 and a second control part operatively connected to the struts 508. This is beneficial as in some situations it is desirable for the distal end of the residual limb to bear no or little weight, and in other situations partial or full end bearing of the residual limb is desired.

The distal support 516 can be substantially non-elastic so that when tension is applied to it, the distal support 516 can transfer a lead to the residual limb. The distal support 516 can provide a cushion and distribution of pressure at the distal end of the residual limb. The distal support 516 can be any suitable member but is shown as a knitted, woven, or netted structure. The distal support 516 can include one or more segments 524 forming the netted structure and connected to one or more coupling parts 526 linking the netted structure to the tensioning elements 534. The tightening system 530 can thus proportionally adjust the fit of the system 500 in different areas of the system 500.

FIG. 27 is a schematic illustration of an adjustable socket system 600 including a tightening system 630. The system 600 includes a distal portion 602, a proximal portion 604, and a plurality struts 608 connected to the distal portion 602 and generally extending between the distal portion 602 and the proximal portion 604.

Similar to the other embodiments, the struts 608 can move radially inward and/or outward to vary a receiving volume 614 adapted to receive a residual limb. For instance, the struts 608 can be movable between an expanded configuration in which one or more portions of the struts 608 move radially outward to loosen the fit of the system 600 on a residual limb inserted in the receiving volume 614, and a closed configuration in which one or more portions of the struts 608 move radially inward to tighten the fit of the system 600 on the residual limb.

Similar to the other embodiments, the tightening system 630 is operatively coupled to the struts 608 and can vary tension applied to the struts 608 to adjust or control the fit of the system 600 and loading of the residual limb. The tightening system 630 includes a tensioning control mechanism 632 that is operable to proportionally or differentially adjust the loading or fit of the system 600 in two or more different areas. The tensioning control mechanism 632 includes a first control part 634 operatively connected to a first area 614A of the receiving volume 614, and a second control part 635 operatively connected to a second area 614B of the receiving volume 614. The first control part 634 and the second control part 635 can be operatively connected. The first control part 634 can be operably independent from the second control part 635 such that the first area 614A can be controlled or adjusted independent of the second area 614B.

In an embodiment, the tensioning control mechanism 632 can control or fine-tune the fit or loading of the system 600 in the first area 614A and in the second area 614B. For instance, the first and second control parts 634, 635 of the tensioning control mechanism 632 can be operated to load the residual limb more in the first area 614A than the second area 614B. The first control part 634 can be operated to increase the tension applied to the struts 608 in the first area 614A (tightening the system 600 in the first area 614A) and/or the second control part 635 can be operated to decrease the tension applied to the struts 608 in the second area 614B (loosening the system 600 in the second area 614B). This advantageously gives a user or clinician greater control over the fit of the system 600 on a residual limb by allowing them to control the proportion of loading by the tightening system 630 in the different areas.

According to a variation, the tightening system 630 can include a feedback feature for communicating fitting or other information to a user or clinician. For example, the dial indicator 638 can display numbers corresponding with displacement and/or tension applied to the struts 608. The dial indicator 638 can display overall displacement and/or tension applied to the struts 608. The dial indicator 638 can display displacement and/or tension of the struts 608 in the first area 614A or the second area 614B. For instance, the dial indicator 638 can include a switch mechanism to change output readings of the dial indicator between the first area 614A and the second area 614B. In other embodiments, the dial indicator 638 can display tension levels in tensioning elements associated with the tightening system 630. This provides a user or clinician a simple and convenient indicator of how secure a fit between the system 600 and a residual limb may be at any given time.

FIG. 28 is another schematic of an adjustable socket system 700 including a tightening system 730 arranged to control or adjust the fit of the system 700 in three different areas. The system 700 is similar to the system 600 except that the tightening system 730 includes a tensioning control mechanism 732 having a first control part 734, a second control part 736, and a third control part 738. The first control part 734 is operatively connected to a first area 714A of a receiving volume 714 defined by struts 708 and arranged to receive residual limb. The second control part 736 is operatively connected to a second area 714B of the receiving volume 714. The third control part 738 is operatively connected to a third area 714C of the receiving volume 714. The control parts 734, 736, 738 can be operatively connected.

The control parts 734, 736, 738 can be independently operable, permitting the tightening system 730 to control or adjust the proportion of load applied to the residual limb in the different areas 714A, 714B, 714C of the receiving volume 714. For instance, the tensioning control mechanism 732 can be operated to tighten the fit of the system 700 in the first area 714A, loosen the fit of the system 700 in the second area 714B, and tighten the fit of the system 700 in the third area 714C. In other embodiments, the tensioning control mechanism 732 can be operated to loosen the fit of the system 700 n the first area 714A, tighten the fit of the system 700 in the second area 714B, and tighten the fit of the system 700 in the third area 714C. It will be appreciated that the control parts 734 can be operated in different combinations. In other embodiments, the tensioning control mechanism 732 can differentially control the fit of the system 700 in the different areas. The tightening system 730 thus gives a user or clinician greater control over the fit and/or tightness of the system 700 on a residual limb.

According to a variation, a feedback feature for communicating information to a user or clinician comprises a set of light emitting diodes 740. If pressure and/or displacement of the system 700 in one or more of the areas 714A, 714B, 714C is good, the feedback feature can illuminate a green LED 740A, communicating that the fit is good. If pressure and/or displacement in one or more of the areas 714A, 714B, 714C is okay, the feedback feature can illuminate a yellow LED 740B, communicating that the fit is okay. If pressure or displacement in one or more of the areas 714A, 714B, 714C is bad, the feedback feature can illuminate a red LED 740C, communicating that the fit is bad. In other embodiments, the feedback feature can communicate information related to the entire receiving volume 714. In other embodiments, the feedback feature can communicate information related to a single or selected ones of the areas 714A, 714B, and 714C. In other embodiments, each LED 740 can be associated with one of the areas 714A, 714B, 714C and arranged to illuminate when the fit in the respective area is good. In other embodiments, the feedback feature can comprise the tensioning control mechanism clicking or tapping when tension or displacement in struts exceeds a target value, providing audio and/or tactile feedback to a user.

FIGS. 29-31 show different embodiments of the tensioning control mechanism for varying and controlling the load imparted to a residual limb in different areas of the adjustable socket system. It will be appreciated that the tensioning control mechanism embodiments described herein can be used alone or in combination with one or more features included in other embodiments of the present disclosure.

As shown in the example in FIG. 29, a tensioning control mechanism 750 includes a first tensioning element 752, a second tensioning element 754, a base 756, a first spool 758, and a second spool 760. The first and second spools 758, 760 can be situated within the base 756 such that the spools 758, 760 are rotatable about an axis 764 relative to the base 756. The first tensioning element 752 can be rotatably linked to the first spool 758 and operatively connected to a first area (e.g., first area 614A) of an adjustable socket system. The second tensioning element 754 can be rotatably linked to the second spool 760 and operatively connected to a second area (e.g., second area 614B) of the adjustable socket system.

When the first spool 758 rotates in a first direction, the first tensioning element 752 is drawn into the base 756 and wound around the spool 758. As the first tensioning element 752 is wound around the first spool 758, tension in the first tensioning element 752 increases, tightening the fit of the adjustable socket system in the first area. When the first spool 758 rotates in a second direction opposite the first direction, the first tensioning element 752 unwinds from the first spool 758 and at least a portion of the first tensioning element 752 exits the base 756. As the first tensioning element 752 unwinds from the first spool 758, tension in the first tensioning element 752 decreases, loosening the fit of the adjustable socket system in the first area.

When the second spool 760 rotates in a first direction, the second tensioning element 754 is drawn into the base 756 and wound around the second spool 760. As the second tensioning element 754 is wound around the second spool 760, tension in the second tensioning element 754 increases, tightening the fit of the adjustable socket system in the second area. When the second spool 760 rotates in a second direction opposite the first direction, the second tensioning element 754 unwinds from the second spool 760 and at least a portion of the second tensioning element 754 exits the base 756. As the second tensioning element 754 unwinds from the second spool 760, tension in the second tensioning element 754 decreases, loosening the fit of the adjustable socket system in the first area.

Optionally, the first and second spools 758, 760 can be rotated via a controller 762. The controller 762 can be attached to the base 756 such that the controller 762 can rotate about the axis 764 relative to the base 756. In an embodiment, the controller 762 can be arranged to rotate the first and second spools 756, 758 together. For instance, an input force (e.g., torque) applied to the controller 762 can be transferred to the first spool 758, which, in turn, can be transferred to the second spool 760. As such, a single input force applied to the controller 762 can adjust the fit in the first and second areas of the adjustable socket system.

In other embodiments, the controller 762 is arranged to rotate the first and second spools 756, 758 independently. For instance, the controller 762 can be rotated by a user in a first setting to adjust the tension in the first tensioning element 752 or can be rotated by the user in a second setting to adjust the tension in the second tensioning element 754. This advantageously can allow a user to vary loading of a residual limb in different areas of the system using a single tensioning control mechanism. The controller 762 is shown as a dial but can be a pull cord, a lever, a handle, or any other suitable mechanism.

FIG. 30 shows another embodiment of a tensioning control mechanism 770 configured to differentially or proportionally vary loading of a residual limb in different areas of an adjustable socket system. The tensioning control mechanism 770 can be similar to the tensioning control mechanism 750 including a first tensioning element 772, a second tensioning element 774, a base 776, a first control part or first spool 778, and a second control part or second spool 780. The first and second spools 778, 780 can be situated within the base 776 such that the spools 778, 780 are rotatable about an axis 784 relative to the base 776. The first tensioning element 772 can be rotatably linked to the first spool 778 and operatively connected to a first area (e.g., 614B). The second tensioning element 774 can be rotatably linked to the second spool 780 and operatively connected to a second area (e.g., 614A).

The tensioning control mechanism 770 includes a gear assembly 786 is arranged to vary the speed, torque, and/or rotational direction of the second spool 780 relative to the first spool 778. The gear assembly 786 comprises a gear member 788 positioned between the first and second spools 778, 780. The gear member 788 includes a first set of teeth 790 arranged to mesh with a corresponding set of teeth 792 on the first spool 778 and a second set of teeth 794 arranged to mesh with a second set of teeth 796 on the second spool 780. The gear member 788 is shown as a bevel gear member but can be any suitable gear member.

To adjust the tension in the first and second tensioning elements 772, 774, a controller 782 is rotated at a first speed relative to the base 776. This rotation of the controller 782 rotates the first spool 778 at the first speed with the controller 782, which, in turn, generates a first tension in the first tensioning element 772. Rotation of the first spool 778 drives rotation of the gear member 788 at a second speed, which, in turn, drives rotation of the second spool 780 at a third speed, generating a second tension in the second tensioning element 774. When the first rotation speed of the first spool 778 is different than the third rotation speed of the second spool 780, the output torque from the first spool 778 is different than the output torque from the second spool 780, making the first and second tensions different. This allows the tensioning control mechanism 770 to differentially tension struts in the first and second areas of the adjustable socket system, which, in turn, loads a residual limb in the first and second areas differently. As such, the tightening system can better control or customize the fit of the adjustable socket system.

The difference between the first and second tensions can be at least in part defined by the size of the gear member 788 and/or spools 778, 780, and/or interaction between the gear member 788 and the spools 778, 780. The length, angle, depth, thickness, curvature, pressure, angle, and/or pitch of the teeth 794 can at least in part define a change in speed, torque, and/or direction in the second spool 780, resulting in a different tension in the second tensioning element. This advantageously can allow a user to differentially or proportionally control the fit of the adjustable socket system in different areas via a single action or twist of the controller 782. For instance, the gear assembly 786 can be arranged so that one complete turn of the controller 782 tightens a first area (e.g., proximal area) about two times, about three times, or about four times more than a second area (e.g., distal area).

According to a variation, the gear assembly 786 can be arranged to convert a smaller input force applied to the controller 782 into a larger output force transferred to the second tensioning element 774 by the second spool 780. This allows a user to load or tighten the adjustable socket system with less strength or dexterity, making the adjustable socket system easier to use and adjust. The controller 782 can be a dial, a pull cord, a lever, a cable, or any other suitable mechanism.

FIG. 31 shows a tensioning control mechanism 830 according to another embodiment. The tensioning control mechanism 830 can be similar to the tensioning control mechanism 770 except that it includes another gear assembly 832 interposed between the controller 782 and the first spool 778. This advantageously allows a user or clinician to differentially tension or tighten different parts of a socket. The gear assembly 832 can be similar to the gear assembly 786 and arranged to vary the speed and/or torque of the first spool 778 relative to the controller 782. For example, when the controller 782 is smaller than the gear assembly 832, the output torque transferred from the second gear assembly 832 to the first spool 778 is greater than the input torque applied to the controller 782 by a user or clinician, providing a mechanical advantage.

According to variation, the gear assembly 786 and/or gear assembly 832 can include at least one end stop 834 arranged to limit relative rotation between the first and second spools 778, 780 and the controller 782, which, in turn, can limit tension applied to the different areas of the adjustable socket system. The at least one end stop 834 can be adjustable.

In an embodiment, the gear assemblies 786, 832 can be adjustable or customizable to vary the load or fit in one or more different areas of the adjustable socket system. For instance, a clinician may interchange, reposition, or change the sizes of the gear assemblies 786, 832 to adjust the speed ratio or gear ratio between the first and second spools 778, 780, which, in turn, varies the tensions applied to the first and second areas by the first and second tensioning elements 772, 774. It will be appreciated that while the tensioning control mechanism is shown including two spools, in other embodiments, the embodiments of the tensioning control mechanism can include one, three, four, or any other suitable number of spools.

FIG. 32 shows a tensioning control mechanism 835 according to another embodiment. The tensioning control mechanism 835 includes a first tensioning element 836, a second tensioning element 838, a base 840, a first control part comprising a first spool 842, a second control part comprising a second spool 844, and a controller 846. The first tensioning element 836 can be rotatably linked to the first spool 842 and operatively connected to a first area (e.g., a proximal area) of the receiving space. The second tensioning element 838 can be rotatably linked to the second spool 844 and operatively connected to a second area (e.g., a distal area) of the receiving space.

The controller 836 is arranged so that it can switch between rotating the first spool 842 and the second spool 844. The controller 836 is shown as a collar member but can be any suitable member. The controller 836 defines a first plurality of teeth 846 that can selectively mesh with a second plurality of teeth 848 defined on the outer surface of the first spool 842 and with a third plurality of teeth 849 defined on the outer surface of the second spool 844. The controller 836 is arranged to translate on the base 840 between the first spool 842 and the second spool 844. To drive rotation of the first spool 842, the controller 836 can be translated in a first direction into engagement with the first spool 842 and rotated relative to the base 840. To drive rotation of the second spool 844, the controller 836 can be translated in a second direction opposite the first direction into engagement with the second spool 844 and rotated.

FIGS. 33 and 34 show an adjustable socket system 850 including a tightening system 852 according to another embodiment. The system 850 includes a distal portion 802, a proximal portion 804, and a plurality of struts 808 connected to the distal portion 802 and generally extending between the distal portion 802 and the proximal portion 804. At least some of the struts 808 are radially adjustable to vary a receiving volume 814 adapted to receive a user's residual limb. The struts 808 can be movable between an expanded configuration in which at least some of the struts 808 are moved radially outward to loosen the fit of the system 800 on a residual limb inserted in the receiving volume 814, and a closed configuration in which at least some of the struts 808 are moved radially inward to tighten the fit of the system 800 on the residual limb.

The tightening system is arranged to move the struts 808 of the system 850 between the expanded and closed configurations. The tightening system 852 includes a tensioning control mechanism 856 disposed in a base 866 of the distal portion 802 and a controller 854 arranged to control the tensioning control mechanism 856. The controller 854 can be any suitable mechanism but is shown as a crank handle 854 attached to the base 866.

The crank handle 854 can be rotatably attached to the base 866 via a pivot point 862. The pivot point 862 can comprise a hinged connection or pivot connection. The crank handle 854 can be removably attached to the base 866. For instance, the crank handle 854 can be arranged to snap in and out of a receiving space defined in the base 866 and provide access to the tensioning control mechanism 856. This can allow the crank handle 854 to be attached for fitting and removed after fitting.

The tensioning control mechanism 856 can be similar to other tensioning control mechanism embodiments previously described including a tensioning element 858 rotatably linked to a spool 860 and operatively connected to the struts 808. When the spool 860 rotates in a first direction, the tensioning element 858 is wound around the spool 860, which, in turn, increases tension in the tensioning element 858. This applies tension to the struts 808, moving the struts 808 toward the closed configuration and tightening the fit of the system 850 on the residual limb. When the spool rotates in a second direction opposite the first direction, the tensioning element 858 unwinds from the spool 860. This decreases tension in the tensioning element 858, allowing the struts 808 to move toward the expanded configuration and loosening the fit of the system 850 on the residual limb.

As seen in FIG. 34, the crank handle 854 is arranged to drive rotation of the spool 860 in the first and second directions. A distal end portion of the crank handle 854 can define a gear portion 864 arranged to mesh or engage with a plurality of teeth 865 defined on the outer surface of the spool 860. The gear portion 864 can be any suitable gear portion but is shown as a worm gear or screw gear, creating a significant mechanical advantage. This advantageously allows a user to adjust the tightness of the system 800 with less strength and/or dexterity because a smaller input force on the crank handle 854 from a user can generate a larger output force from the spool 860 and therefore tension in the struts 808.

When the crank handle 854 is rotated in a clockwise direction, the gear portion 864 of the handle feature 854 drives the spool 860 to rotate in the first direction, moving the struts 808 toward the closed configuration. When the crank handle 854 is rotated in a counter-clockwise direction, the gear portion 864 drives the spool 860 to rotate in the second direction, moving the struts 808 toward the expanded configuration. In other embodiments, rotation of the crank handle 854 in the counter-clockwise direction drives the spool 860 to rotate in the first direction and rotation in the clockwise direction drives the spool 860 to rotate in the second direction.

Because of the shear friction and/or mechanical advantage in the interaction between the gear portion 864 and the spool 860, the tightening system 852 can be self-locking. In other words, an input force or torque applied to the spool 860 will not move the crank handle 854. Thus, whatever tension is set by the crank handle 854 remains substantially fixed until the crank handle 854 is readjusted.

Figure 36:
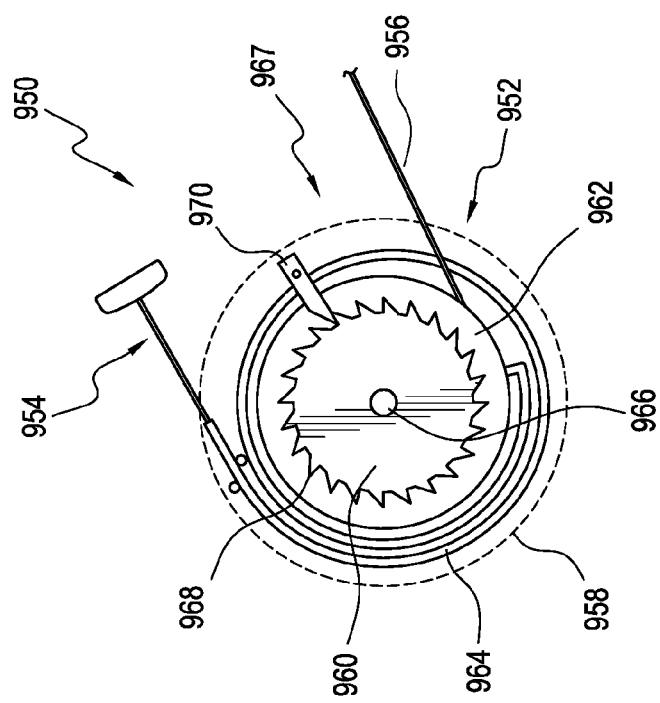
FIG. 36 is a schematic view of the tightening system in FIG. 35.
Figure 35:
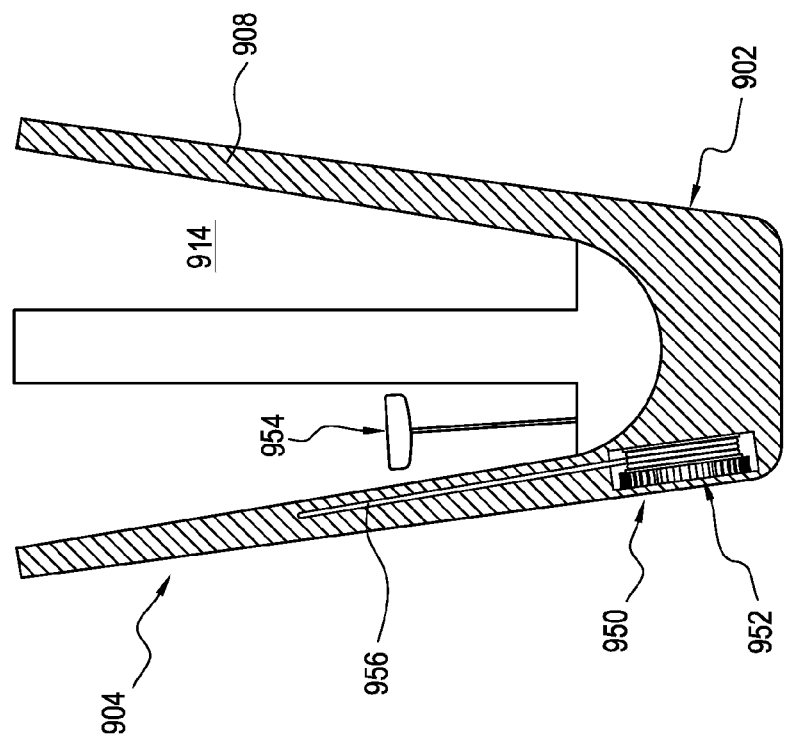
FIG. 35 is a cross section view of an adjustable socket system including a tightening system according to another embodiment.

FIGS. 35 and 36 show another embodiment of an adjustable socket system 900 including a tightening system 950. The system 900 includes a distal portion 902, a proximal portion 904, and a plurality of struts 908 connected to the distal portion 902 and generally extending between the distal portion 902 and the proximal portion 904. At least some of the struts 908 are radially adjustable to vary a receiving volume 914 adapted to receive a residual limb. The struts 908 are movable between an expanded configuration in which at least some of the struts 908 are moved radially outward to loosen the fit of the system 950, and a closed configuration in which at least some of the struts 908 are moved radially inward to tighten the fit of the system 950 on the residual limb.

The tightening system 950 is arranged to move the struts 908 of the system 950 between the closed and expanded configurations. The tightening system 950 includes a tensioning control mechanism 952 and a controller 954 operatively connected to the tensioning control mechanism 952. The tensioning control mechanism 952 can be similar to other tension control mechanism embodiments previously described including a tensioning element 956, a base 958, a spool 960, a disc 962, and a spring 964 attached to the disc 962. The tensioning element 956 is rotatably linked to the spool 960 and operatively connected to the struts 908. The spool 960 and the disc 962 can be situated within the base 958 such that they are rotatable about an axis 966 relative to the base 958.

The tensioning control mechanism 952 includes a ratcheting mechanism 967 comprising a plurality of teeth 968 defined on an outer surface of the spool 960 and a pawl 970 pivotally attached to the base 958 or the disc 962. The ratcheting mechanism 967 allows the spool 960 and the disc 962 to rotate together in the first direction but prevents the spool 960 from rotating a second direction opposite the first direction such that the disc 962 rotates in the second direction relative to the spool 960.

The controller 954 can comprise an elongate element 972 including a distal end attached to the spring 964 and a proximal free end including a soft grip 974. The elongate element 972 can comprise a cord, wire, line, or other suitable element. The controller 954 can be arranged such that it can be attached to the struts 908 or the distal portion 902 for storage during use of the system 900. In other embodiments, the controller 954 can be arranged to be tucked inside of the struts 908 for storage during use of the system 900. While a single tensioning control mechanism 952 and controller 954 are shown, it will be appreciated that the system 900 can include two, three, or four or any other suitable number of tensioning control mechanisms. For instance, each strut 908 can include a tensioning control mechanism operatively connected to the controller 954.

When the controller 954 is tensioned, the spring 964 is tensioned, which, in turn, causes the spring 962 to coil around the disc 962 and then stretch or elongate, storing energy. The tension in the spring 962 in turn rotates the disc 962 in the first direction. This beneficially can assist a user in tensioning the controller 954, making the system 950 easier to use for users who may have limited strength or dexterity.

As the disc 962 rotates in the first direction, the pawl 970 is arranged to slide up and over the teeth 968 of the spool 960 so that the spool 960 rotates with the disc 962 in the first direction. Rotation of the spool 960 in the first direction causes the tensioning element 956 to wind around the spool 960, tensioning the tensioning element 956 and struts 908 toward the closed configuration, tightening the fit of the system 950 on a residual limb.

When the controller 954 is released, stored energy in the spring 964 causes the spring 964 to reverse its direction, which, in turn, rotates the disc 962 in the second direction and recoils the spring 962. When the disc 962 rotates in the second direction, the pawl 970 is arranged to lock against the teeth 968 so that the spool 960 is prevented from rotating with the disc 962 in the second direction. As such, the tensioning element 956 remains wound around the spool 960 as the spring 964 recoils on the disc 962. The pawl 970 can be manually disengaged from the teeth 968 so that the tensioning element 956 can be unwound from the spool 960, permitting the struts 908 to return toward the expanded configuration and loosening the fit of the system 950 on the residual limb.

FIGS. 37-43 show other embodiments the adjustable socket system including tightening systems arranged to automatically tighten and loosen the fit of the adjustable socket system when the system is loaded and unloaded by a user. It will be appreciated that these systems can be similar to and can include many of the same or similar features of the other adjustable socket systems described herein.

As shown in the example of FIGS. 37 and 38, an adjustable socket system 1000 can comprise a distal portion 1002, a proximal portion 1004, and an axis 1006 extending between the distal and proximal portions 1002, 1004. A plurality of elongated struts 1008 are connected to the distal portion 1002 and extend between the distal portion 1002 and the proximal portion 1004. The distal portion 1002 can include a base 1020 and a distal support 1022 proximal to the base 1020. The distal support 1022 is adapted to receive and support a distal end of the residual limb inserted in the receiving volume 1014. The distal support 1022 can have a cup-like configuration. The distal support 1022 is arranged to move along the axis 1006 relative to the base 1020. A base connector 1025 is secured to a bottom portion of the base 1020, and is adapted to connect to prosthetic components.

The struts 1008 at least in part define a receiving volume 1014 adapted to receive a residual limb. Similar to the other embodiments, one or more portions of the struts 1008 can move radially inward and/or outward to vary the receiving volume 1014. In an embodiment, the struts 1008 are movable between a relaxed or expanded configuration (shown in FIG. 37) in which portions of the struts 1008 are moved away from the axis 1006 to loosen the fit of the system 1000 on the residual limb, and a closed configuration (shown in FIG. 38) in which portions of the struts 1008 are moved toward the axis 1006 from the expanded configuration to tighten the fit of the system 1000 on the residual limb. Each strut 1008 includes a distal end and a proximal free end 1012.

A tightening system 1050 includes an actuating part 1022 arranged to move the struts 1008 of the system 1000 between the expanded configuration and the closed configuration in response to loading and unloading of the system 1000. The actuating part 1022 can include the distal support 1022.

When the system 1000 is not in use, the struts 1008 can assume the expanded configuration, allowing a residual limb to be easily inserted into and removed from the receiving volume 1014.

When the residual limb inserted in the receiving volume and a distal end portion of the residual limb applies a load or pressure to the distal support 1022, the tightening system 1050 automatically moves the struts 1008 toward the closed configuration. This tightens the fit of the system 1000 on the residual limb in proportion to the load or pressure applied to the distal support 1022.

The tightening system 1050 thus advantageously permits the system 1000 to "relax" and be looser when the user is inactive (e.g., sitting or lying down) and become tighter when walking, and become very tight during sports. It also permits the system 1000 to tighten or clamp onto the residual limb during stance and loosen during swing, thus optimally using cyclic loading to best load the residual limb. The tightening system 1050 can be an alternative to or used in combination with other tightening systems described herein. For instance, the system 1000 can include the tightening system 1050 for providing a primary tightening of the system 1000 and the tightening system 180 or the tightening system 130 for providing a secondary tightening of the system 1000.

It will be appreciated that the load applied by the user's residual limb, the position of the struts 1008 in the closed configuration, and/or the fit of the system 1000 can be selected or adjusted based on one or more criteria such as, for example, activity level, physical characteristics of the residual limb, and/or treatment protocols, making the system 1000 more versatile, and easy to fit to a user.

In an embodiment, the tightening system 1050 comprises a first part 1024 of the strut 1008 that extends upward and radially outward from the base 1020 to a first connection point 1026 where it connects to a second part 1028. From the first connection point 1026, the second part 1028 extends radially inward and upward to a second connection point 1034 where the second part 1028 attaches to the distal support 1022. From the second connection point 1034, each strut 1008 extends generally upward and radially outward. The first connection point 1026 or the second connection point 1034 can define a pivot point. The pivot point can be hinged or pin connection.

With the struts 1008 in the expanded configuration, a user can load the distal support 1022, moving the distal support 1022 downward along the axis 1006 toward the base 1020. This downward movement of the distal support 1022 rotates the struts 108 toward the axis 1006, decreasing the receiving volume 1014. In the illustrated embodiment, downward movement of the distal support 1022 causes the second part 1028 to rotate in a first direction about the first connection point 1026, moving the proximal ends 1012 of the struts 1008 toward the axis 1006 and decreasing the receiving volume 1014. This allows the weight or load of the user on the distal support 1022 to automatically tighten the system 1000 on the residual limb. Moreover, the tightening of the system 1000 is proportional to the load.

When the distal support 1022 is unloaded, the distal support 1022 can move upward away from the base 1020. This upward movement rotates the proximal ends 1012 of the struts 108 away from the axis 1006, returning the system 1000 toward the expanded configuration and decreasing the receiving volume 1014. Thus, the unloading of the distal support 1022 can loosen the fit of the system 1000 on the residual limb.

According to a variation, a biasing mechanism 1036 can be situated between the base 1020 and the distal support 1022. The biasing mechanism 1036 is adapted to bias the struts 1008 toward the expanded configuration. The biasing mechanism 1036 can be a spring mechanism, a resilient foam member, or any other suitable resilient member. When the distal support 1022 is loaded, the biasing mechanism 1036 can be compressed as the distal support 1022 moves toward the base 1020. When the distal support is unloaded or the load is reduced, stored energy in the biasing mechanism 1036 can tend to drive the distal support 1022 away from the base 1020.

According to a variation, the first part 1024 can be fixedly connected to the second part 1028 at the first connection point 1026. When the distal support 1022 is unloaded, the inherent properties of the struts 1008 can help move the struts 1008 toward the expanded configuration. To meet the stiffness/flexibility, strength, and weight requirements needed for use on the system 1000, the struts 1008 can be made of a stiff, but elastically bendable or deformable material, such as carbon fiber, plastic, or metal.

FIGS. 39 and 40 illustrate another embodiment of an adjustable socket system 1100 with a tightening system 1150 that tightens and/or loosens the system 1100 in response to loading and unloading of the system 1100. The system 1100 can be similar to and can include many of the same or similar features as any of the other adjustable socket systems described herein.

The system 1100 includes a distal portion 1102, a proximal portion 1104, and an axis 1106 extending between the distal and proximal portions 1102, 1104. A plurality of struts 1108 are connected to the distal portion 1102 and generally extend between the distal portion 1102 and the proximal portion 1104. The struts 1108 at least in part define a receiving volume 1114 adapted to receive a residual limb. The struts 1108 can rotate radially inward and/or outward to vary the receiving volume 1114 or expand a circumference of the system 1100. The struts 1108 are movable between a relaxed or expanded configuration in which portions of the struts 1108 are moved away from the axis 1106 to loosen the fit of the system 1100 on a residual limb inserted in the receiving volume 1114, and a closed configuration in which portions of the struts 1108 are moved radially inward toward the axis 1106 from the expanded configuration to tighten the fit of the system 1100 on the residual limb. Each strut 1108 includes a distal end 1110 and a proximal free end 1112.

The struts 1108 are arranged to rotate relative to the axis 1106 via a connection point 1130 at or near the distal end 1110. The connection point 1130 can comprise a pinned or hinged connection connecting the distal end 1110 to a proximal portion of a respective support member described below.

In an embodiment, the struts 1108 can include a distal part 1144 defining the distal end 1110 and a proximal part 1146 defining the proximal end 1112. According to a variation, the proximal part 1146 can be removably attached to the distal part 1144. This beneficially allows the proximal parts 1146 to be interchanged with different proximal parts 1146 of varying lengths or widths to adjust the height or fit of the struts 1108. This also allows the proximal parts 1146 to be removed for repair or replacement without having to replace the entire strut 1108 of system 1100. The proximal parts 1146 can be removably attached to the distal parts 1144 via one or more fasteners 1148.

The distal portion 1102 can include a base 1120 and a distal support 1122 proximal to the base 1120. The distal support 1122 is arranged to move along the axis 1106 relative to the base 1120. The distal support 1122 can have a cup-like configuration. The base 1120 includes a base plate 1124 and a plurality of generally upright support members 1126 distributed circumferentially about the base plate 1124 and the distal support 1122. The base 1120 includes a base connector 1125 adapted to connect to prosthetic components.

The tightening system 1150 includes an actuating part 1121 arranged to move the struts 1108 of the system 1100 between the expanded and closed configurations in response to load and unloading of the system 1100.

The actuating part 1121 can comprise the distal support 1122. A plurality of teeth 1128 are defined on an outer surface of the distal support 1122. The teeth 1128 can extend circumferentially about the distal support 1122. The distal end 1110 of the struts 1108 can define a plurality of teeth 1140 arranged to mesh with the teeth 1128 of the distal support 1122. The distal end 1110 can have a cylindrical or convex shape. The teeth 1140 can extend across a width of the distal end 1110. The teeth 1140 can be generally linear. The teeth 1140 can be generally helical. The distal end 1110 can include between about 4 and about 12 teeth, about 5 teeth and about 11 teeth, or about 6 teeth and about 10 teeth. In other embodiments, the distal end 1110 can include more or less teeth.

The interaction or tooth loads between the distal ends 1110 and the distal support 1122 create a driving force on the struts 1108 as the distal support 1122 moves along the axis 1106 relative to the base 1120. As the distal support 1122 moves up and down relative to the base 1120, the interaction between the teeth 1128, 1140 generates the driving force that in turn rotates the struts 1108 about the connection point 1130, moving the system 1100 between the closed configuration and the expanded configuration. The distal end 1110 can have an enlarged configuration to better accommodate the teeth 1140 and/or the interaction between the distal support 1122 and the struts 1108.

The dimension and configuration of the interaction between the distal support 1122 and the struts 1108 can at least in part define the strength of the tightening system 1150 to maintain the position of the system 1000. For instance, the length, angle, depth, thickness, curvature, pressure angle, and/or pitch of the teeth can in part define the load the strut 1108 can support.

In an embodiment, the teeth 1140 of the strut 1108 are engaged with the teeth 1128 of the distal support 1122 along substantially the entire length of the teeth 1140 extending in a direction across the distal end 1110. This greater contact area helps form a solid connection between the distal support 1122 and the struts 1108, which, in turn, helps the tightening system 1150 to better control movement of the system 1000 between the expanded configuration and closed configuration. As such, the tightening system 1150 can be made simpler. For instance, distal portions of the struts 1108 and/or the distal support 1122 can be made of plastic material or other lightweight material that can resist deformation during use. This can result in adjustable socket systems that are more cost effective to manufacture, less bulky, lighter-weight, and more comfortable to wear. It will be appreciated that that the struts 1108 and/or the base 1120 can be made of metal, plastic material, carbon fiber, combinations thereof, or any other suitable material.

As seen in FIG. 40, with the struts 1108 in the expanded configuration, a user can load the distal support 1122, moving the distal support 1122 downward toward the base 1120. This downward movement of the distal support 1122 causes the struts 1108 to rotate toward the axis 1106 about the connection points 1130, which, in turn tightens the fit of the system 1110 on a residual limb positioned in the receiving space 1114. When the distal support 1122 is unloaded or the load is decreased, the distal support 1122 can move upward and away from the base 1120 along the axis 1106, causing the struts to rotate away from the axis 1106. This loosens the fit of the system 1110 on the residual limb.

According to a variation, a biasing mechanism can bias the struts toward the expanded configuration or closed configuration. For instance, a biasing mechanism 1136 can be situated between the base 1120 and the distal support 1122 that is arranged to bias the system 1110 toward the expanded configuration when the distal support 1122 is unloaded or a load on the distal support 1122 decreases. It should be appreciated that the biasing mechanism can be any suitable member.

FIGS. 41-43 illustrate another embodiment of an adjustable socket system 1200 with a tightening system 1250 arranged to tighten and/or loosen the system 1200 in response to loading and unloading of the system 1200. The system 1200 can be similar to and can include many of the same or similar features as any of the other adjustable socket systems described herein. Moreover, it will be appreciated that the tightening system 1250 can be used alone or in combination with other tightening systems. For instance, the system 1200 can include the tightening system 1250 and the tightening system 130.

The system 1200 includes a distal portion 1202, a proximal portion 1204, and an axis 1206 extending between the distal and proximal portions 1202, 1204. A plurality of struts 1208 are connected to the distal portion 1202 and extend generally between the distal portion 1202 and the proximal portion 1204. The struts 1208 at least in part defined a receiving volume 1214 arranged to receive a residual limb therein. The struts 1208 are movable between a relaxed or expanded configuration in which portions of the struts 1208 are moved away from the axis 1206 to loosen the fit of the system 1200 on the residual limb, and a closed configuration in which the portions of the struts 1208 are moved toward the axis 1206 to tighten the fit of the system 1200 on a residual limb inserted in the receiving volume 1214. Each strut 1208 includes a distal end 1210 and a proximal free end 1212.

The struts 1208 are arranged to rotate relative to the axis 1206 via a connection point 1230 at or near the distal end 1210. The connection point 1230 can comprise a pinned or hinged connection connecting the distal end 1210 of the strut 1208 to the distal portion 1202. According to a variation, the struts 1208 can define a plurality of through holes 1256 formed along a length of the struts 1208. The through holes 1256 can be adapted to help attach textile and/or material to the struts 1208. The through holes 1256 can be adapted to attach one or more tensioning elements described below to the struts 1208.

The distal portion 1202 can include a base 1220, a stem portion 1222 attached to the base 1220, and a distal support 1224 positioned on and arranged to move relative to the stem portion 1222. The distal support 1224 is adapted to receive and support a distal end of the residual limb inserted in the receiving volume 1214. The distal support 1224 can have a cup-like configuration and can define a radial flange 1252 having a plurality of through holes 1254 distributed circumferentially about the flange 1252.

The tightening system 1250 comprises at least one tensioning element 1258 connected between the struts 1208 and an actuating part comprising the distal support 1224. The at least one tensioning element 1258 can be threaded or passed through at least some of the through holes 1254 on the distal support 1124 to connect the at least one tensioning element 1258 to the distal support 1224. The at least one tensioning element 1258 can be threaded or passed through at least some of the through holes 1256 to connect the at least one tensioning element 1258 to the struts 1208. The at least one tensioning element 1258 can be a textile or material segment, a band member, a knitted fabric, lacing, an elastic cord, an elastomer material, and/or any other suitable material.

With the struts 1208 in the expanded configuration, the distal end of a user's residual limb can load the distal support 1224, which, in turn, moves the distal support 1224 downward on the stem portion 1222 toward the base 1220. This downward movement of the distal support 1224 causes the at least one tensioning element 1258 extending between the distal support 1224 and the struts 1208 to tension or pull the struts 1208 radially inward toward the closed configuration, tightening the fit of the system 1200 on the residual limb. When the distal support 1224 is unloaded or the load on the distal support 1224 decreases, the distal support 1224 can move upward on the stem portion 1222 or away from the base 1220. This upward movement of the distal support 1224 reduces tension on the struts 1208 from the at least one tensioning element 1258, allowing the struts 1208 to return to the expanded configuration, loosening the fit of the system 1200.

According to a variation, a biasing mechanism can bias the struts toward the expanded configuration or the closed configuration. For instance, the biasing mechanism can comprise a residual limb. To secure the residual limb within the system 1200, the residual limb may be under some degree of compression. When tension from the at least one tensioning element 1258 is released, the residual limb can expand and push the struts 1208 radially outward toward the expanded configuration. In other embodiments, properties of the at least one tensioning element 1258 can at least in part bias the struts 1208 toward the expanded configuration.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open-ended and have the same meaning as the word "comprising" and variants thereof (e.g., "comprise" and "comprises").

The invention claimed is:

1. An adjustable socket system comprising:
a distal portion including a base, and a proximal portion;
an axis extending between the distal and proximal portions; and
a plurality of struts connected to the distal portion and distributed circumferentially about the axis, the struts at least in part defining a receiving volume adapted to receive a residual limb and movable between an expanded configuration in which at least some of the struts are moved radially outward relative to the axis to loosen the fit of the adjustable socket system, and a closed configuration in which at least some of the struts are moved radially inward relative to the expanded configuration to tighten the fit of the adjustable socket system;
a tightening system operatively connected to the struts and arranged to tighten and loosen the fit of the adjustable socket system on one or more areas of the residual limb, the tightening system including a distal support at or near the base, the distal support being operably connected to the struts and movable along the axis relative to the base to move the struts between the expanded configuration and the closed configuration, wherein an outer surface of the distal support defines a first plurality of teeth, and a distal end of each strut defines a second plurality of teeth arranged to mesh with the first teeth of the distal support, and interaction between the first and second teeth generates a drive force that rotates the struts about a connection between the struts and the base.

2. The adjustable socket system of claim 1, wherein the distal support is adapted to receive and support a distal end of the residual limb inserted in the receiving volume, the struts being arranged to automatically move toward the closed configuration when the distal end of the residual limb applies a load on the distal support.

3. The adjustable socket system of claim 2, wherein the first and second teeth define a geared connection between the distal support and the struts.

4. The adjustable socket system of claim 3, wherein movement of the distal support toward the base drives the struts toward the closed configuration.

5. The adjustable socket system of claim 1, wherein movement of the distal support along the axis drives rotation of the struts about the connection between the struts and the base.

6. The adjustable socket system of claim 1, wherein a biasing mechanism is arranged to bias the struts toward the expanded configuration.

7. The adjustable socket system of claim 6, wherein the biasing mechanism is situated between the base and the distal support.

8. The adjustable socket system of claim 1, wherein the distal support has a cup configuration.

9. The adjustable socket system of claim 1, wherein each strut is connected to the base via a pinned connection.

10. The adjustable socket system of claim 1, wherein the base includes a base plate and a plurality of upright support members distributed circumferentially about the base plate.

11. The adjustable socket system of claim 10, wherein the struts are pivotally connected to the upright support members.

12. An adjustable socket system comprising:
a distal portion including a distal support arranged to support a distal end of a residual limb, and a proximal portion;
an axis extending between the distal and proximal portions; and
a plurality of struts connected to the distal portion and distributed circumferentially about the axis, the struts at least in part defining a receiving volume adapted to receive the residual limb and movable between an expanded configuration in which the struts are moved radially outward relative to the axis to loosen the fit of the adjustable socket system on the residual limb, and a closed configuration in which the struts are moved radially inward relative to the expanded configuration to tighten the fit of the adjustable socket system on the residual limb, the distal support interacting with distal ends of the struts and movable along the axis;
wherein the interaction between the distal support and the distal ends of the struts drives the struts towards the closed configuration when the distal support is loaded and moved along the axis by the residual limb.

13. The adjustable socket system of claim 12, wherein the distal portion includes a base and an actuating part at or near the base, the actuating part being operably connected to the struts and movable along the axis relative to the base to move the struts between the expanded configuration and the closed configuration.

14. The adjustable socket system of claim 13, wherein the load moves the actuating part downwardly along the axis to drive rotation of the struts about a connection point between the struts and the base.

15. The adjustable socket system of claim 13, wherein an outer surface of the actuating part defines a first plurality of teeth, and a distal end of each strut defines a second plurality of teeth arranged to mesh with the first teeth of the distal support.

16. An adjustable socket system comprising:
a distal portion and a proximal portion, the distal portion including a base and an actuating part comprising a distal support at or near the base that is arranged to support a distal end of a residual limb;
an axis extending between the distal and proximal portions; and
a plurality of struts connected to the distal portion and distributed circumferentially about the axis, the struts at least in part defining a receiving volume adapted to receive the residual limb and movable between an expanded configuration in which the struts are moved radially outward relative to the axis to loosen the fit of the adjustable socket system on the residual limb, and a closed configuration in which the struts are moved radially inward relative to the expanded configuration to tighten the fit of the adjustable socket system on the residual limb, the distal support interacting with distal ends of the struts and movable along the axis relative to the base,
wherein the interaction between the distal support and the distal ends of the struts drives the struts towards the closed configuration when the distal support is loaded and moved along the axis by the residual limb.

* * * * *